(12) United States Patent
Gross

(10) Patent No.: US 8,357,176 B2
(45) Date of Patent: Jan. 22, 2013

(54) FIBROID TREATMENT APPARATUS AND METHOD

(75) Inventor: Yossi Gross, Moshav Mazor (IL)

(73) Assignee: Fibro Control, Inc., New Castle, DE (US)

( * ) Notice: Subject to any disclaimer, the term of this patent is extended or adjusted under 35 U.S.C. 154(b) by 893 days.

(21) Appl. No.: 12/374,884

(22) PCT Filed: Jul. 18, 2007

(86) PCT No.: PCT/IL2007/000911
§ 371 (c)(1),
(2), (4) Date: Feb. 24, 2009

(87) PCT Pub. No.: WO2008/012802
PCT Pub. Date: Jan. 31, 2008

(65) Prior Publication Data
US 2009/0318950 A1    Dec. 24, 2009

Related U.S. Application Data

(63) Continuation-in-part of application No. 11/591,044, filed on Oct. 31, 2006.

(60) Provisional application No. 60/820,130, filed on Jul. 24, 2006.

(51) Int. Cl.
*A61M 29/00* (2006.01)
*A61B 19/00* (2006.01)
*A61B 17/42* (2006.01)
*A61B 17/46* (2006.01)
*A61D 1/10* (2006.01)

(52) U.S. Cl. .......................... 606/193; 898/128; 606/119

(58) Field of Classification Search .................. 606/119, 606/191–195; 128/898
See application file for complete search history.

(56) References Cited

U.S. PATENT DOCUMENTS

| 3,730,186 A | 5/1973 | Edmunds, Jr. et al. |
| 4,344,438 A | 8/1982 | Schultz |
| 4,430,076 A | 2/1984 | Harris |
| 4,581,025 A | 4/1986 | Timmermans et al. |
| 4,881,939 A | 11/1989 | Newman |
| 5,001,054 A | 3/1991 | Wagner |
| 5,195,964 A | 3/1993 | Kletzky et al. |

(Continued)

FOREIGN PATENT DOCUMENTS

EP    162982 A2    12/1985
(Continued)

OTHER PUBLICATIONS

An Office Action dated Jul. 20, 2011, which issued during the prosecution of U.S. Appl. No. 11/591,044.

(Continued)

*Primary Examiner* — Gary Jackson
*Assistant Examiner* — Michael Mendoza
(74) *Attorney, Agent, or Firm* — Fish & Richardson P.C.

(57) ABSTRACT

Apparatus is provided, including a tube (22) that is configured to pass into a patient's vagina (26) and to penetrate vaginal tissue (24) until a distal tip (36) of the tube is outside of a uterine artery (28) of the patient, but in a vicinity of a portion (38) of the uterine artery that supplies a uterine fibroid (30). A balloon (40), disposed at the distal tip, is inflated to cause local squeezing of the portion of the uterine artery to an extent sufficient to occlude the uterine artery. Other embodiments are also described.

9 Claims, 19 Drawing Sheets

U.S. PATENT DOCUMENTS

| | | | |
|---|---|---|---|
| 5,338,297 A | 8/1994 | Kocur et al. |
| 5,626,134 A | 5/1997 | Zuckerman |
| 5,688,234 A | 11/1997 | Frisbie |
| 5,766,151 A | 6/1998 | Valley et al. |
| 5,770,454 A | 6/1998 | Essenpreis et al. |
| 5,976,069 A | 11/1999 | Navia et al. |
| 5,979,453 A | 11/1999 | Savage et al. |
| 5,998,204 A | 12/1999 | Tsien et al. |
| 6,004,260 A | 12/1999 | Thompson |
| 6,059,766 A | 5/2000 | Greff |
| 6,163,714 A | 12/2000 | Stanley et al. |
| 6,183,502 B1 | 2/2001 | Takeuchi |
| 6,197,534 B1 | 3/2001 | Lakowicz et al. |
| 6,217,529 B1 | 4/2001 | Wax et al. |
| 6,254,601 B1 | 7/2001 | Burbank et al. |
| 6,264,676 B1 | 7/2001 | Gellman et al. |
| 6,382,214 B1 | 5/2002 | Raz et al. |
| 6,425,867 B1 | 7/2002 | Vaezy et al. |
| 6,521,446 B2 | 2/2003 | Hellinga |
| 6,540,693 B2 | 4/2003 | Burbank et al. |
| 6,550,482 B1 | 4/2003 | Burbank et al. |
| 6,602,251 B2 | 8/2003 | Burbank et al. |
| 6,625,479 B1 | 9/2003 | Weber et al. |
| 6,635,065 B2 | 10/2003 | Burbank et al. |
| 6,638,286 B1 | 10/2003 | Burbank et al. |
| 6,679,851 B2 | 1/2004 | Burbank et al. |
| 6,764,488 B1 | 7/2004 | Burbank et al. |
| 6,905,506 B2 | 6/2005 | Burbank et al. |
| 6,958,044 B2 | 10/2005 | Burbank et al. |
| 7,141,057 B2 | 11/2006 | Burbank et al. |
| 7,172,603 B2 | 2/2007 | Burbank et al. |
| 7,207,996 B2 | 4/2007 | Burbank et al. |
| 7,223,279 B2 | 5/2007 | Burbank et al. |
| 7,229,465 B2 | 6/2007 | Burbank et al. |
| 7,264,596 B2 | 9/2007 | Burbank et al. |
| 7,325,546 B2 | 2/2008 | Burbank et al. |
| 7,329,265 B2 | 2/2008 | Burbank et al. |
| 7,333,844 B2 | 2/2008 | Jones et al. |
| 7,594,890 B2 | 9/2009 | Burbank et al. |
| 2002/0165579 A1 | 11/2002 | Burbank et al. |
| 2002/0188306 A1 | 12/2002 | Burbank et al. |
| 2003/0114878 A1 | 6/2003 | Diederich et al. |
| 2003/0120286 A1 | 6/2003 | Burbank et al. |
| 2003/0120306 A1 | 6/2003 | Burbank et al. |
| 2003/0216759 A1 | 11/2003 | Burbank et al. |
| 2004/0097788 A1 | 5/2004 | Mourlas et al. |
| 2004/0097961 A1 | 5/2004 | Burbank et al. |
| 2004/0097962 A1 | 5/2004 | Burbank et al. |
| 2004/0098035 A1 | 5/2004 | Wada et al. |
| 2004/0117652 A1 | 6/2004 | Burbank et al. |
| 2004/0158262 A1 | 8/2004 | Burbank et al. |
| 2005/0101974 A1 | 5/2005 | Burbank et al. |
| 2005/0113852 A1 | 5/2005 | Burbank et al. |
| 2005/0143674 A1 | 6/2005 | Burbank et al. |
| 2005/0187561 A1 | 8/2005 | Lee-Sepsick et al. |
| 2005/0197594 A1 | 9/2005 | Burbank et al. |
| 2005/0228416 A1 | 10/2005 | Burbank et al. |
| 2005/0245842 A1 | 11/2005 | Burbank et al. |
| 2006/0000479 A9 | 1/2006 | Burbank et al. |
| 2006/0094983 A1 | 5/2006 | Burbank et al. |
| 2006/0106109 A1 | 5/2006 | Burbank et al. |
| 2006/0178698 A1 | 8/2006 | McIntyre et al. |
| 2006/0241337 A1 | 10/2006 | Jones et al. |
| 2007/0049973 A1 | 3/2007 | Burbank et al. |
| 2007/0173863 A1 | 7/2007 | Burbank et al. |
| 2007/0203505 A1 | 8/2007 | Burbank et al. |
| 2007/0265613 A1 | 11/2007 | Edelstein et al. |
| 2008/0039888 A1 | 2/2008 | Doare et al. |
| 2008/0188863 A1 | 8/2008 | Chu |
| 2008/0200924 A1 | 8/2008 | Burbank et al. |
| 2009/0043295 A1 | 2/2009 | Arnal et al. |
| 2009/0054916 A1 | 2/2009 | Meier et al. |
| 2009/0093758 A1 | 4/2009 | Gross |
| 2009/0287088 A1 | 11/2009 | Burbank et al. |

FOREIGN PATENT DOCUMENTS

| | | |
|---|---|---|
| GB | 2302025 A | 1/1997 |
| JP | 5177001 A | 7/1993 |
| JP | 10229986 A | 9/1998 |
| WO | 97/17105 A1 | 5/1997 |
| WO | WO0033724 A3 | 8/2000 |
| WO | 0180713 A2 | 11/2001 |
| WO | 02078521 A2 | 10/2002 |
| WO | 02078522 A2 | 10/2002 |
| WO | 02078549 A2 | 10/2002 |
| WO | WO02051320 A3 | 10/2002 |
| WO | 02100286 A1 | 12/2002 |
| WO | 03007827 A1 | 1/2003 |
| WO | 2004045420 A2 | 6/2004 |
| WO | 2004045422 A2 | 6/2004 |
| WO | 2004045426 A1 | 6/2004 |
| WO | 2004045430 A2 | 6/2004 |
| WO | 2004069025 A2 | 8/2004 |
| WO | WO2005051211 A1 | 6/2005 |
| WO | 2006086234 A2 | 8/2006 |
| WO | 2007027392 A1 | 3/2007 |
| WO | 2008012802 A2 | 1/2008 |

OTHER PUBLICATIONS

"Abdominal hysterectomy: a new approach for young gynaecologists," by Dutta, J Indian Med Assoc. Oct. 1997;95 (10):556-8. (an abstract).

"A model for studying chronic reduction in uterine blood flow in pregnant sheep," by Clark et al., Am J Physiol Heart Circ Physiol242: H297-H301, 1982.

"A modified technique for hemostasis during myomectomy," by DeLancey, Surgery Gynecology and Obstetrics, 1992, vol. 174, Pt 2, pp. 153-154.

"An in vivo study ofthe effects of ischaemia on uterine contraction, intracellular pH and metabolites in the rat," by Harrison et al., Journal ofPhysiology (1994), 476.2, pp. 349-354.

"Cervical ectopic pregnancy," by Rahimi et al., J Am Assoc Gynecol Laparosc. Aug. 1996;3(4, Supplement):S41 (an abstract).

"Cervical pregnancy: three case reports and a review ofthe literature," by Van de Meerssche et al., Hum Reprod. Jul. 1995;10(7):1850-5 (an abstract).

"Uterine artery ligation in the control ofpostcesarean hemorrhage," by O'Leary, J Reprod Med. Mar. 1995;40(3):189-93 (an abstract).

"Common hepatic artery pseudoaneurysm secondary to pancreatitis," by Fava et al., SurgEndosc (1994) 8:1223-1226.

"Devascularization of craniofacial tumors by percutaneous tumor puncture," by Cacasco et al., AJNR Am J Neuroradiol15:1233-1239, Aug. 1994.

"Embolization ofuterine leiomyomata: current concepts in management," Braude et al., Human Reproduction Update 2000, vol. 6, No. 6, pp. 603-608.

"Experience with internal iliac artery ligation in obstetrics and gynaecological practice," by Jain, J Indian Med Assoc. Sep. 1990;88(9):246-7 (an abstract).

"Extraperitoneal Laparoscopic Hysterectomy for Fibroid Uteri," by Kadar, JAm Assoc Gynecol Laparosc. Aug. 1996;3(4, supplement):S20 (an abstract).

"Indications for Hysterectomy: Have They Changed," by Steege, Clinical Obstetrics and Gynecology:vol. 40(4) Dec. 1997pp. 878-885.

"Laparoscopic Uterine Artery Ligation for Treatment of Symptomatic Adenomyosis," by Wang et al., Presented at the 10th annual congress of the International Society for Gynecologic Endoscopy, Chicago, Illinois, Mar. 28-31, 2001 (an abstract).

The Journal ofthe American Association of Gynecologic Laparoscopists vol. 9, Issue 2, May 2002, pp. 191-198, by Lichtinger, Presented at the 30th annual meeting ofthe American Association of Gynecologic Laparoscopists, San Francisco, California, Nov. 16-19, 2001. (an abstract).

"Ligation of uterine arteries, per vaginum, in a case ofrecurrent secondary post partum haemorrhage following caesarean section," by Ross, Aust. N.Z.J. Obstet. Gynaec. (1965) 5:215.

"Own experience with internal iliac and ovarian artery ligation in gynecological and oncological surgeries," by Neuberg, Ginekol Pol. May 1998;69(5):358-62 (an abstract).

"Pelvic anatomy of the ureter in relation to surgery performed through the vagina," by Hofineister, Clinical Obstetrics and Gynecology, vol. 25, No. 4, Dec. 1982.

"Preliminary experience with uterine artery ligation for symptomatic uterine leiomyomas," by Lee et al., Journal of the American Association of Gynecologic Laparoscopists, Aug. 1999, vol. 6, No. 3.

"The management of uterine leiomyomas," by Lefebvre et al., SOGC Clinical Practice Guidelines, No. 128, May 2003.

"Therapeutic embolization with detachable silicone balloons. Early clinical experience," by White et al., JAMA. Mar. 23, 1979;241(12):1257-60 (an abstract).

"Treatment outcomes of uterine artery embolization and laparoscopic uterine artery ligation for uterine myoma," by Park et al., Yonsei Medical Journal vol. 44, No. 4, pp. 694-702, 2003.

"Two uterine arterial management methods in laparoscopic hysterectomy," by Song et al., J Obstet Gynaecol Res. Apr. 1998;24(2):145-51 (an abstract).

"Use of a large Foley catheter balloon to control postpartum hemorrhage resulting from a low placental implantation. A report of two cases," by Bowen et al., J Reprod Med. Aug. 1985;30(8):623-5 (an abstract).

"Uterine artery embolization: An underused method of controlling pelvic hemorrhage," by Vedantham et al., American Journal of Obstetrics & Gynecology Apr. 1997, 176:4.

"Vaginal uterine artery ligation avoids high blood loss and puerperal hysterectomy in postpartum hemorrhage," by Hebisch et al., Obstetrics & Gynecology vol. 100, No. 3, Sep. 2002.

"Uterine artery occlusion by embolization or surgery for the treatment of fibroids: a unifying hypothesis—transient uterine ischemia," by Burbank et al., Journal of the American Association of Gynecologic Laparoscopists, Nov. 2007, vol. 7, No. 4.

"Vaginal ligature of uterine arteries during postpartum hemorrhage," by Philippe et al., International Journal of Gynecology and Obstetrics 56 (1997) 267-270.

P. Turkewitsch, "The synthesis of fluorescent chemosensors responsive to cAMP and other nucleotides", Montreal Quebec, Sep. 1998.

G. Gilardi, et al., "Spectroscopic properties of an engineered maltose binding protein", Protein Engineering vol. 10 No. 5, pp. 479-486, 1997.

Homme W. Hellinga, et al., "Protein engineering and the development of generic biosensors", TffiTECH Apr. 1998, vol. 16.

S.P.J. Higson, et al., "Biosensors: a viable monitoring technology?", Med. &Biol. Eng. & Comput., 1994,32,601-609.

Leah Tolosa, et al., "Optical assay for glucose based on the luminescnence decay time of the long wavelength dye Cy5•", Sensors and Actuators B 45 (1997) 93-99.

Leah Tolosa, et al., "Glucose sensor for low-cost lifetime-based sensing using a genetically-engineered protein", Analytical Biochemistry 267, 114-120 (1999).

K. Yamada, et al., "Measurement of glucose uptake and intracellular calcium concentration in single, living pancreatic~-cells", The Journal of Biological Chemistry, vol. 275, No. 29, Jul. 2000, pp. 22278-22283.

Leah Tolosa, et al., "Lifetime-based sensing of glucose using energy transfer with a long lifetime donor", Analytical Biochemistry 250, 102-108, 1997.

J.C. Pickup, et al., "Fluorescence-based glucose sensors", Biosensors and Bioelectronics 20 (2005) 2555-2565.

M. Sakurada, et al., "Relation between glucose-stimulated insulin secretion and intracellular calcium accumulation studied with a superfusion system of a glucoseresponsive pancreatic~-celliine MIN6", Endo. 1993, vol. 132, No. 6.

J.S. Marvin, et al., "The rational design of allosteric interactions in a monomeric protein and its applications to the construction of biosensors", Proc. Natl. Acad. Sci. USA vol. 94, pp. 4366-4371, Apr. 1, 1997.

H.J. Philippe, et al., "Vaginal ligature of uterine arteries during postpartum hemorrhage", International Journal of Gynecology & Obstetrics 56 (1997) 267-270.

An Office Action dated Jan. 20, 2012, which issued during the prosecution of U.S. Appl. No. 11/591,044.

An Office Action dated Jan. 5, 2011, which issued during the prosecution of Applicant's U.S. Appl. No. 11/591,044.

An International Search Report and a Written Opinion, both dated Jan. 20, 2011, which issued during the prosecution of Applicant's PCT/IL10/00610.

An English translation of an Office Action mailed Jun. 19, 2012, which issued during the prosecution of Japanese Patent Application No. 2009-521412.

An Office Action dated Jul. 27, 2012, which issued during the prosecution of U.S. Appl. No. 12/509,732.

An office action dated Sep. 25, 2012, which issued during the prosecution of U.S. Appl. No. 11/591,044.

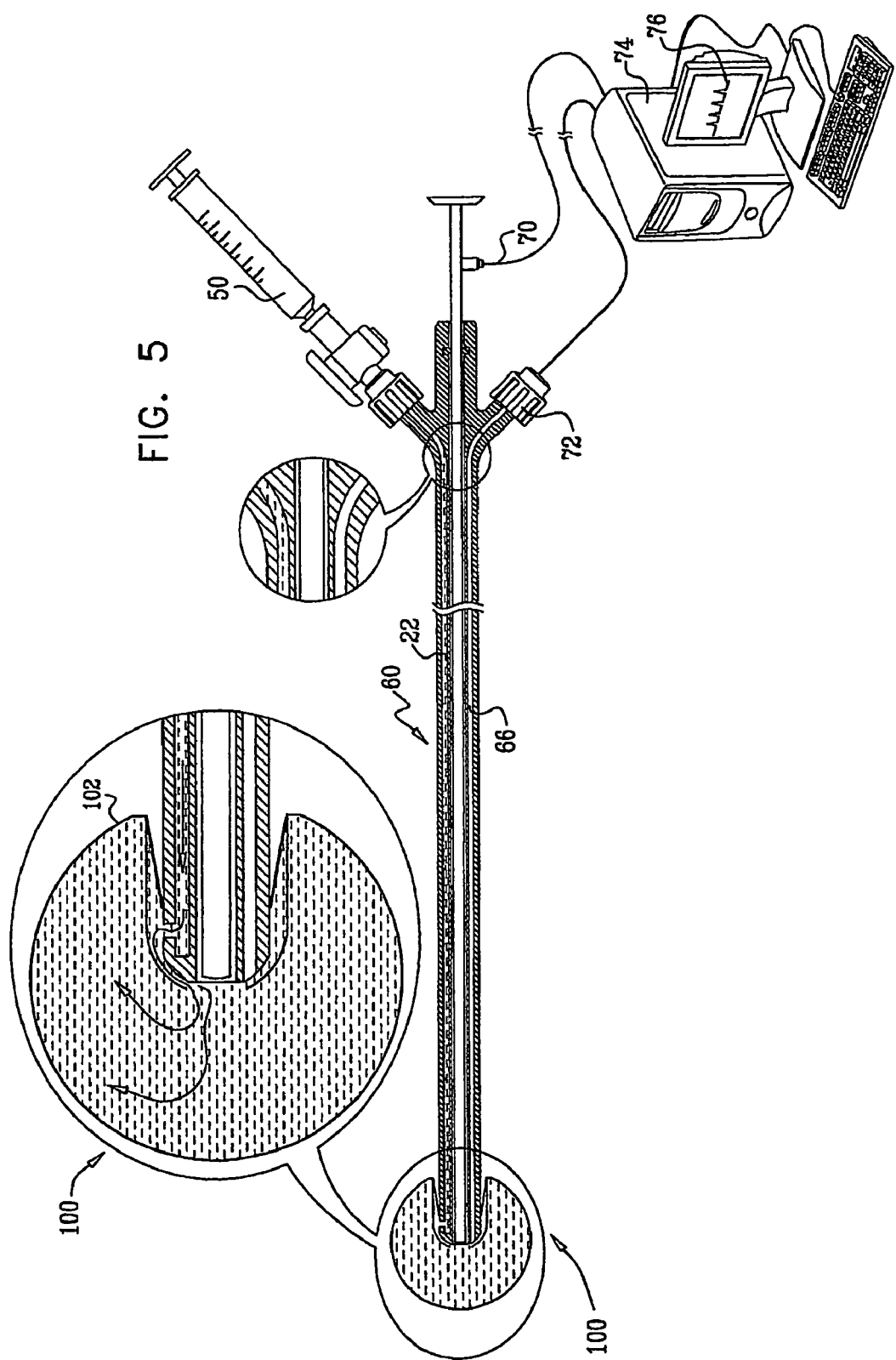

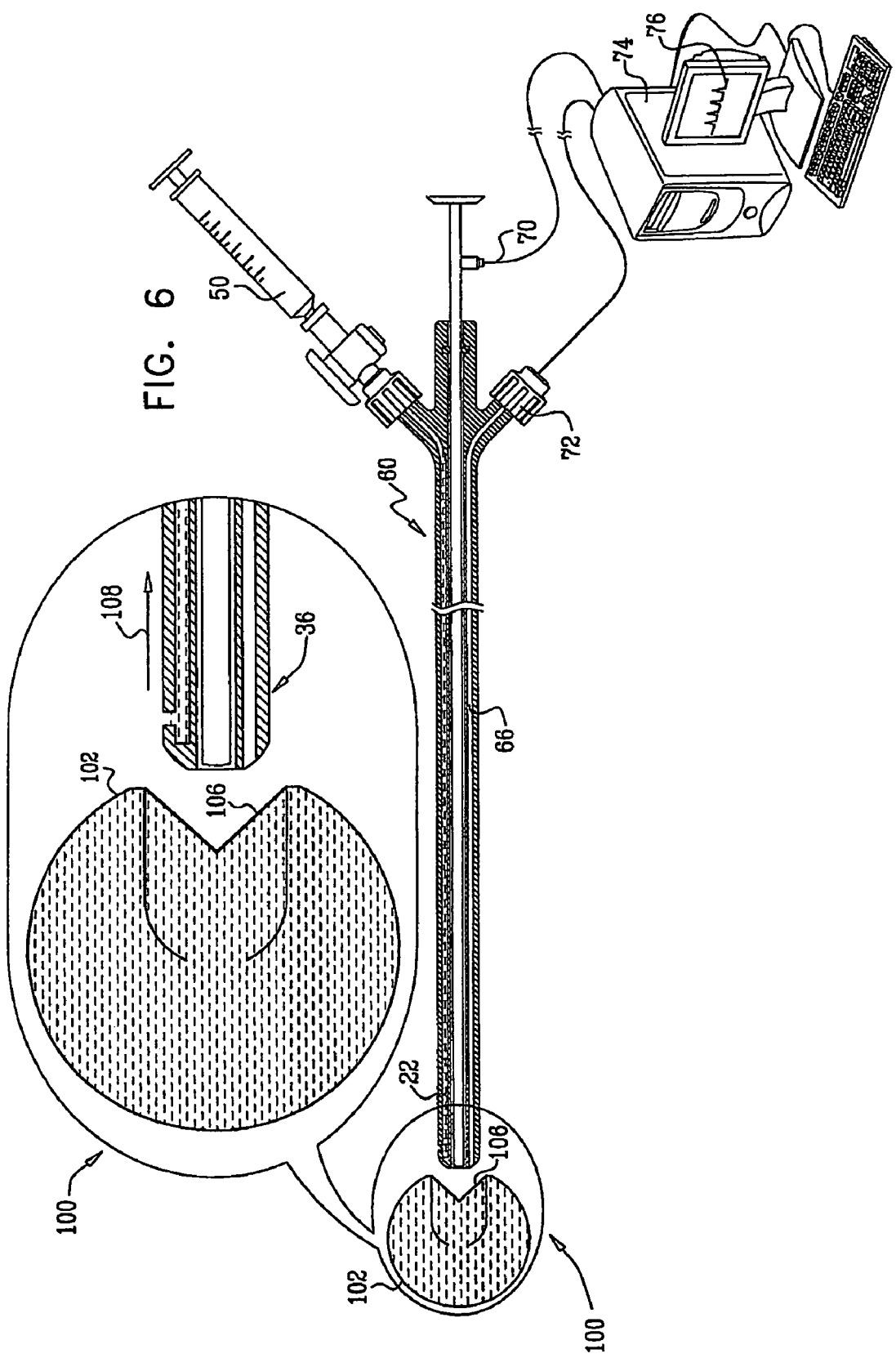

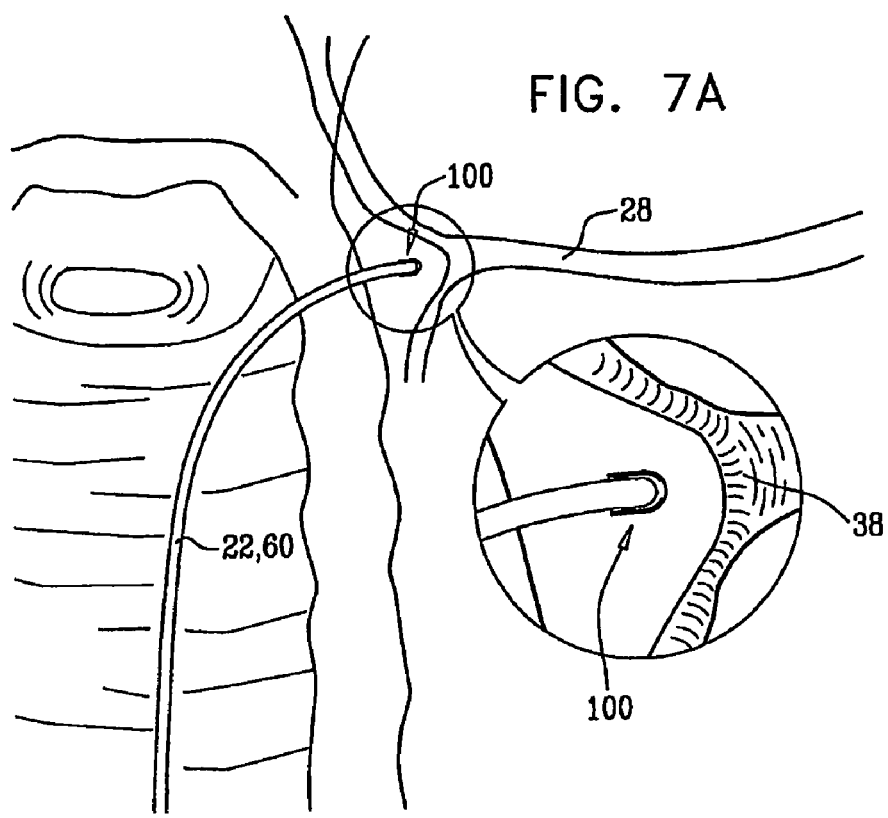
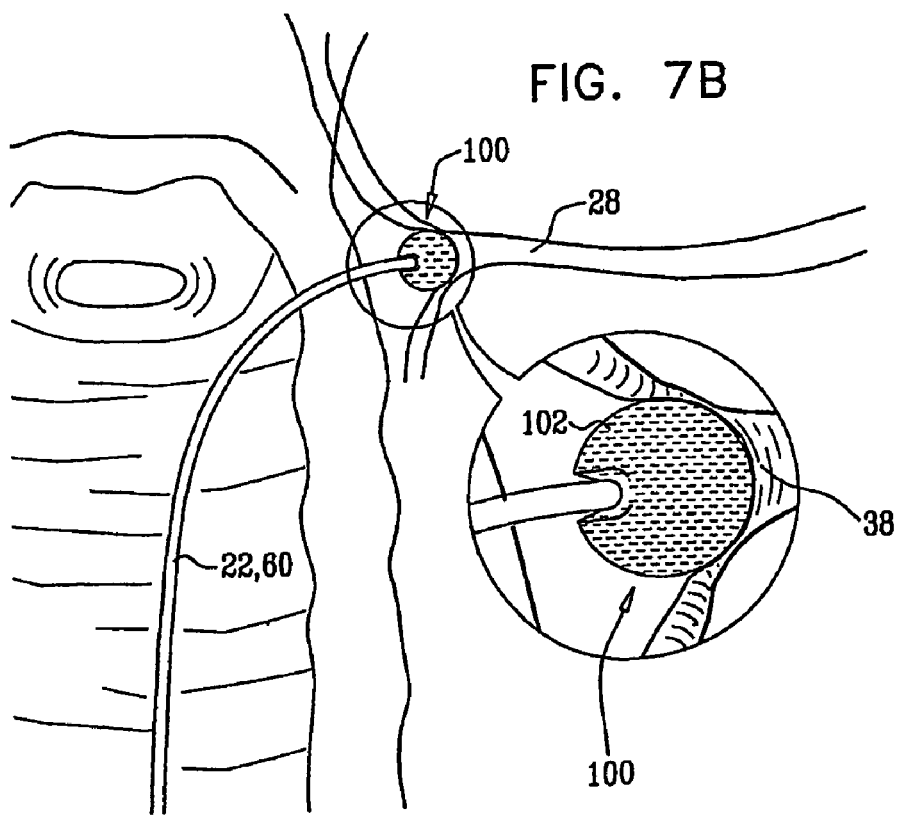

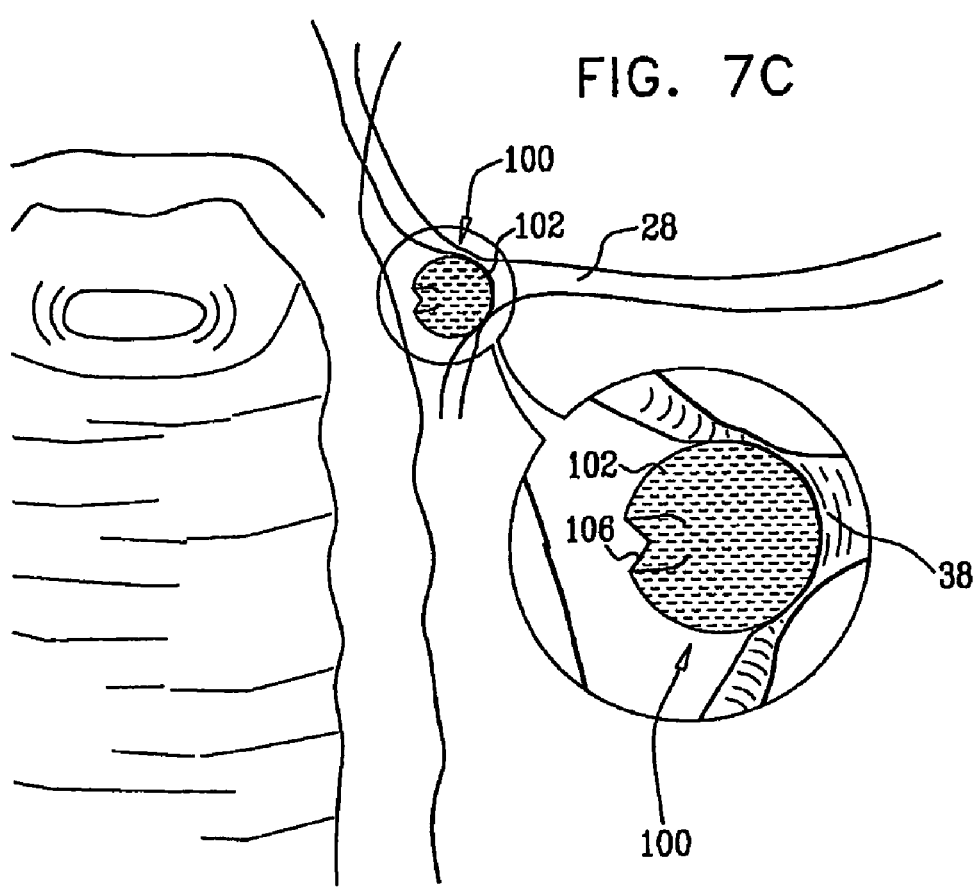

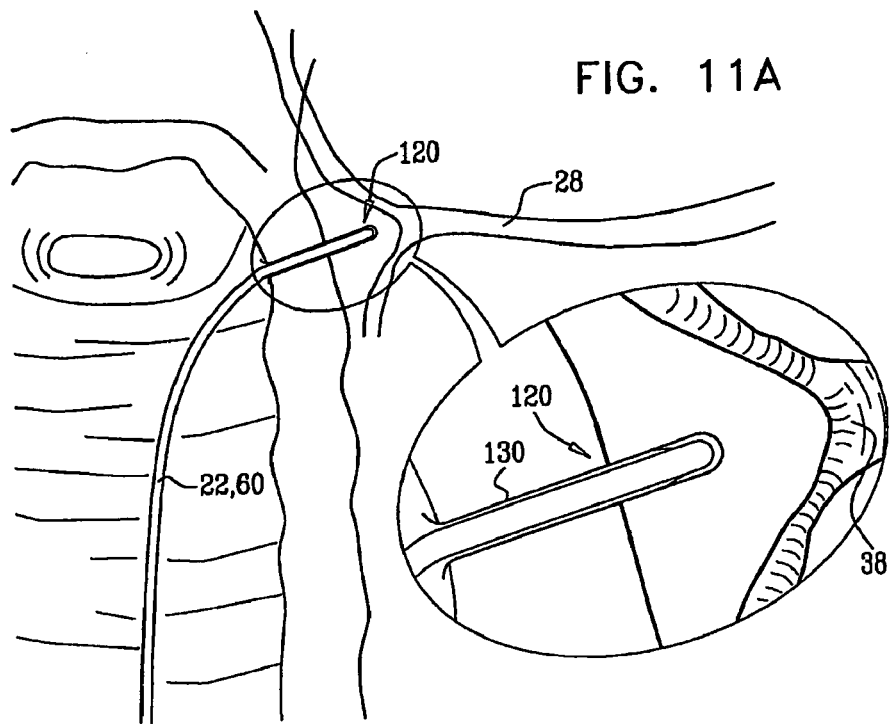
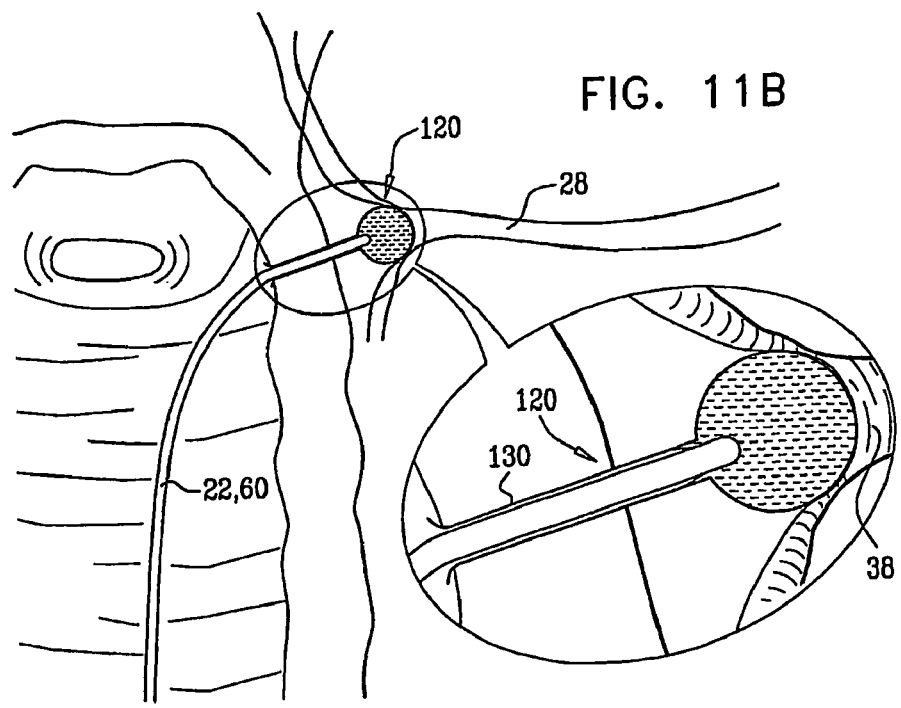

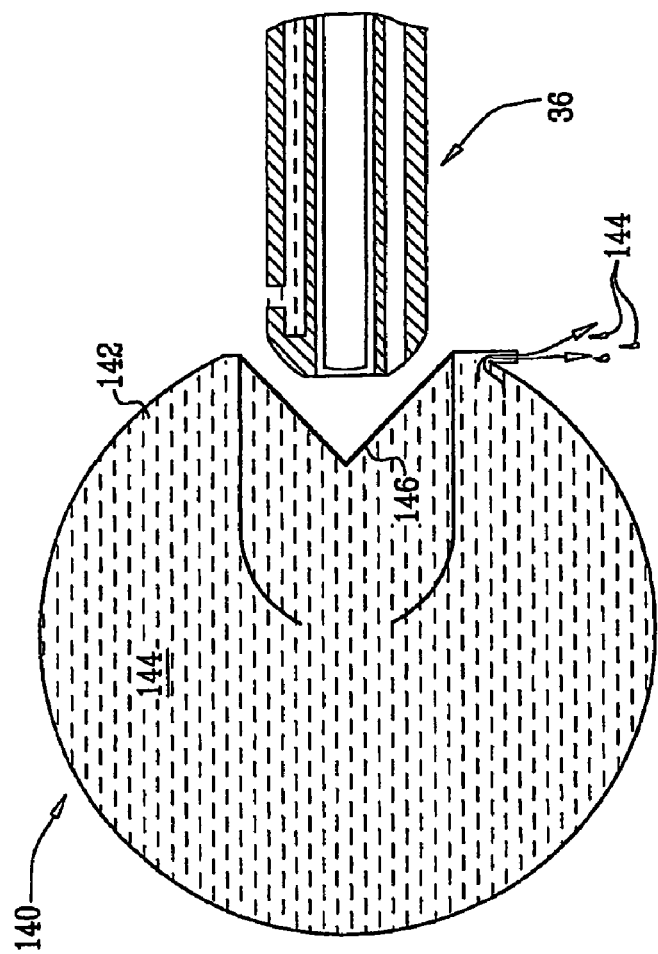
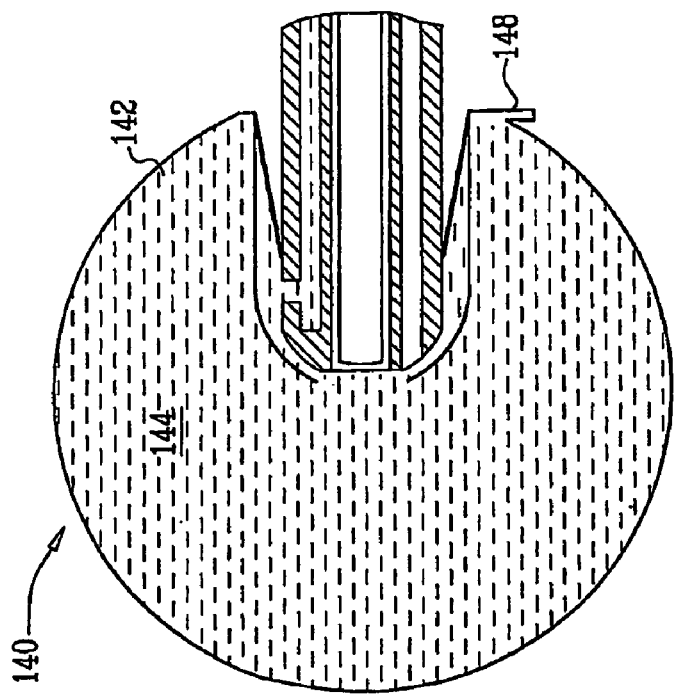
FIG. 12B
FIG. 12A

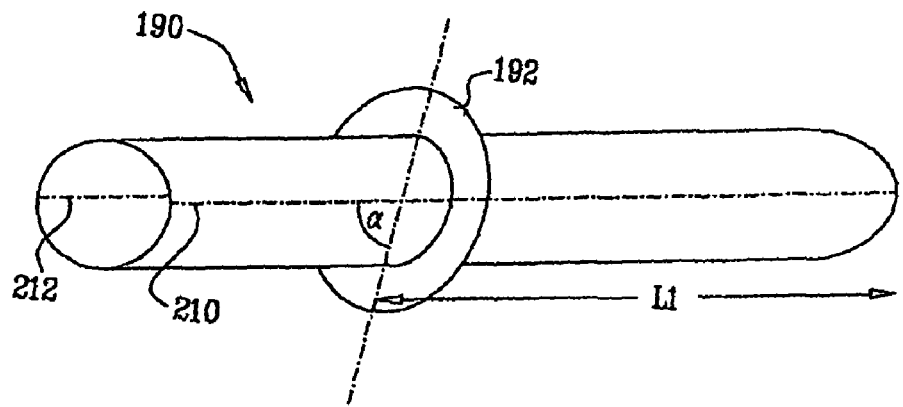
FIG. 14D
FIG. 15
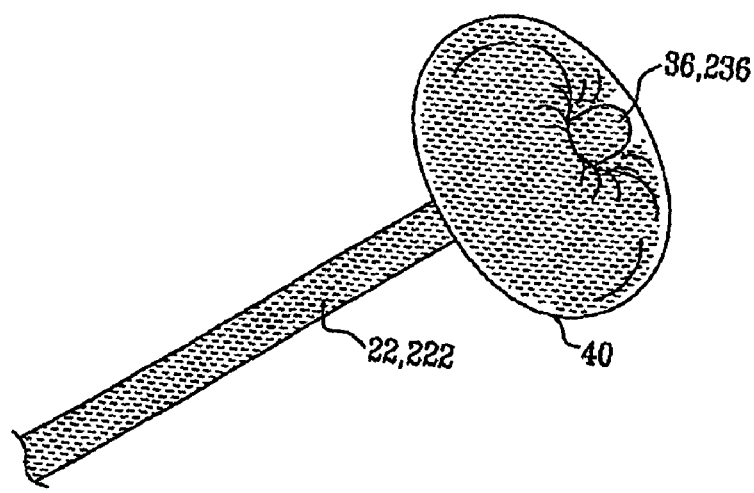

FIBROID TREATMENT APPARATUS AND METHOD

CROSS REFERENCE TO PRIOR APPLICATIONS

The present application is a U.S. national phase application under 35 U.S.C. §371 of International Patent Application No. PCT/IL2007/000911 to Gross, filed Jul. 18, 2007, which claims priority from and is a continuation-in-part of U.S. patent application Ser. No. 11/591,044 to Gross, filed Oct. 31, 2006, entitled, "Fibroid treatment apparatus and method," which claims priority from U.S. Provisional Patent Application 60/820,130 to Gross, filed Jul. 24, 2006, entitled, "Fibroid treatment apparatus and method." All of the above applications are incorporated herein by reference. The International Application published in English on Jan. 31, 2008 as WO 2008/012802 under PCT Article 21(2).

FIELD OF THE INVENTION

The present invention relates generally to treatment of fibroids, and, specifically, to reduction of fibroids by uterine artery occlusion.

BACKGROUND OF THE INVENTION

Uterine fibroids are benign tumors of muscle and connective tissue that develop within, or are attached to, the uterine wall.

Vascular Control Systems (San Juan Capistrano, Calif.) has developed a device called the Flostat. According to the company, the primary element of the Flostat system is a Doppler guided clamp designed for bilateral temporary occlusion of the uterine arteries. The device is currently indicated for use during conservative gynecologic procedures such as laparoscopic myomectomy.

U.S. Pat. No. 6,764,488 to Burbank et al., U.S. Pat. No. 6,254,601 to Burbank et al., U.S. Pat. No. 6,602,251 to Burbank et al., and US Patent Application Publication 2003/0216759 to Burbank et al., which are incorporated herein by reference, describe devices and methods for treating a uterine pathology which receives its blood supply from a uterine artery. In particular, uterine fibroids are described as being effectively treated by occluding the uterine arteries using trans-vaginal, trans-uterine, transrectal, or retroperitoneal approaches. The devices and methods are intended for performance by a patient's gynecologist in the course of treatment, avoiding the need for (a) referrals to specialist practitioners and (b) other treatments, such as hysterectomy. The methods include both temporary and permanent occlusion of the arteries. A cannula carries an imaging device and a member which penetrates tissue, the member including a device which partially or completely, and temporarily or permanently, occludes a uterine artery.

US Patent Application Publication 2005/0113852 to Burbank et al., which is incorporated herein by reference, describes an intravaginal uterine artery occlusion device for treating uterine disorders such as fibroids, dysfunctional uterine bleeding, postpartum hemorrhage and the like. An occlusion device has a cervical receptacle or cap with an open distal end for receiving the patient's uterine cervix and an elongated shaft having a distal end secured to the closed proximal end of the cervical receptacle and an inner lumen extending to the distal end of the elongated shaft. The patient's uterine cervix is held within the interior of the receptacle by the application of a vacuum to the interior of the receptacle through the inner lumen of the shaft or otherwise, while the leading edge(s) of the cervical receptacle press against the patient's vaginal formix to occlude an underlying or adjacent uterine artery. At least one blood flow sensor may be provided on the leading edge of the receptacle to aid in locating a uterine artery and to monitor blood flow through the located uterine artery. FIG. 7 of the '852 publication illustrates the device positioned within the patient, with a side expansion balloon expanded inwardly to press against the vaginal formix to ensure the occlusion of the patient's left uterine artery.

US Patent Application Publication 2006/0000479 to Burbank et al., which is incorporated herein by reference, describes non-permanent occlusion of the uterine arteries as being sufficient to cause the demise of uterine myomata without unnecessarily exposing other tissues and anatomical structures to hypoxia attendant to prior permanent occlusion techniques. A therapeutically effective transient time of occlusion of a uterine artery to treat uterine fibroid tumors is from 1 hours to 24 hours, and preferably is at least about 4 hours. A therapeutically effective temporary time of occlusion of a uterine artery to treat uterine fibroid tumors is from 1 day (24 hours) to 7 days (168 hours), and preferably is about 4 days (96 hours). By invaginating the tissues of the vaginal wall up to or around a uterine artery, collapse of the uterine artery is described as being achievable without penetrating tissue of the patient.

US Patent Application Publication 2004/0097788 to Mourlas et al., which is incorporated herein by reference, describes apparatus for locating morphological features within a body cavity. The apparatus includes a catheter including proximal and distal ends, a transparent balloon carried on the distal end, and an optical imaging assembly carried on the distal end for imaging through the balloon. The balloon includes a channel extending therethrough to a lumen extending through the catheter. A guidewire or other localization member is received in the lumen that is extendable through the channel. During use, the catheter is inserted into a right atrium of a heart, and the balloon is expanded and placed against the wall of the heart to locate the coronary sinus. Sufficient force is applied to clear blood between the surface and the wall and clear the field of view of the imaging assembly. The catheter is manipulated to locate the coronary sinus, whereupon the localization member is advanced into the coronary sinus.

PCT Publication WO 06/086234 to McIntyre et al., which is incorporated herein by reference, describes a method for treating a uterine fibroid comprising forming an incision in a vaginal formix to expose a first blood vessel supplying the fibroid, forming an opening in the first blood vessel and inserting an introducer into the first blood vessel via the opening in combination with the steps of advancing a catheter to a desired position within the first blood vessel via the introducer and introducing an occlusive agent into the first blood vessel through the catheter to block blood flow through the first blood vessel. A device for treating uterine fibroids comprises an elongated sheath sized for insertion into uterine arteries via an incision in the vaginal formix, the sheath including a sheath lumen extending from a first sheath opening formed in a proximal end of the sheath to a second sheath opening formed in a distal end of the sheath and a body, a distal end of which is connected to the proximal end of the sheath, the body including a body lumen extending therethrough from a first body opening at a proximal end of the body and a second body opening at the distal end thereof, the second body lumen communicating with the sheath lumen in combination with a hemostatic valve controlling the flow of blood through the body lumen.

The following patents and patent applications, which are incorporated herein by reference, may be of interest:
U.S. Pat. No. 7,229,465 to Burbank et al.
U.S. Pat. No. 7,223,279 to Burbank et al.
U.S. Pat. No. 7,207,996 to Burbank et al.
U.S. Pat. No. 7,172,603 to Burbank et al.
U.S. Pat. No. 7,141,057 to Burbank et al.
U.S. Pat. No. 6,905,506 to Burbank et al.
U.S. Pat. No. 6,638,286 to Burbank et al.
U.S. Pat. No. 6,635,065 to Burbank et al.
U.S. Pat. No. 6,550,482 to Burbank et al.

SUMMARY OF THE INVENTION

In some embodiments of the present invention, apparatus for treating a patient's uterine fibroid comprises a tube, configured to be passed into the patient's vagina. The tube penetrates vaginal tissue until a distal tip of the tube is outside of a uterine artery of the patient, but in a vicinity of a portion of the uterine artery that supplies the fibroid. A balloon is configured to be disposed at the distal tip, and to be inflated to cause local squeezing of the portion of the uterine artery to an extent sufficient to occlude the uterine artery.

Although some patients or physicians may choose to carry out embodiments of the present invention in conjunction with lumbar puncture, some embodiments of the present invention do not require lumbar puncture, and, indeed, allow the patient to move around in bed or be completely mobile while the balloon is squeezing the uterine artery.

There is therefore provided, in accordance with an embodiment of the present invention, apparatus including:

a tube, configured to be passed into a patient's vagina and to penetrate vaginal tissue until a distal tip of the tube is outside of a uterine artery of the patient, but in a vicinity of a portion of the uterine artery that supplies a uterine fibroid; and a balloon, configured to be disposed at the distal tip and to be inflated to cause local squeezing of the portion of the uterine artery to an extent sufficient to occlude the uterine artery.

In an embodiment, the balloon is configured to be disposed at a distance of less than 4 cm from the portion of the uterine artery to cause the local squeezing of the portion of the uterine artery.

In an embodiment, the balloon has a toroidal shape, and is configured to be wrapped around the distal tip of the tube.

In an embodiment, the tube is configured to reside in part within the patient's vagina throughout the time that the balloon is causing the local squeezing, and is configured to facilitate extraction of the balloon from the patient.

In an embodiment, the tube includes a flexible tube.

In an embodiment, the apparatus includes a plug disposed at a proximal end of the tube.

In an embodiment, the apparatus includes a syringe and a syringe needle, which are configured to pierce the plug and inflate the balloon via the tube, and the plug is configured to seal itself subsequent to withdrawal of the syringe.

In an embodiment, the apparatus includes an introducer configured to be passed into a patient's vagina and to penetrate vaginal tissue until a distal tip of the introducer is at the site, and the tube is configured to pass through the vaginal tissue, via the introducer, until the distal tip of the tube is at the site.

In an embodiment, the introducer includes a metal.

In an embodiment, the apparatus includes a pharmaceutical-administration tube configured for placement within the introducer and configured to facilitate administration to the patient of a pharmaceutical product.

In an embodiment, the apparatus includes a pharmaceutical-administration tube configured for placement within the introducer and configured to facilitate administration to the patient of an anesthetic.

In an embodiment, the apparatus includes a pharmaceutical-administration tube configured for placement within the introducer and configured to facilitate administration to the patient of a pharmaceutical product selected from the group consisting of: an anti-inflammatory agent, and an antibiotic.

In an embodiment, the introducer includes a stopper configured to stop the penetration of the vaginal wall by the introducer when the distal tip of the introducer is disposed at the site.

In an embodiment, the stopper is disposed at an angle of between 45 degrees and 85 degrees from a longitudinal axis of the introducer.

In an embodiment, the stopper is disposed at an angle of between 75 degrees and 85 degrees from a longitudinal axis of the introducer.

In an embodiment, the stopper is disposed at a distance of between 1 cm and 2 cm from the distal tip of the introducer.

In an embodiment, the tube includes a marker configured to indicate when the distal tip of the tube is disposed at the site.

In an embodiment, the marker is configured to be adjacent to a proximal end of the introducer when the distal tip of the tube is disposed at the site.

In an embodiment, the tube is configured to reside in part within the patient's vagina throughout the time that the balloon is causing the local squeezing, and is configured to facilitate extraction of the balloon from the patient.

In an embodiment, the introducer is configured to be split and to be removed from the patient when the distal tip of the tube is at the site.

In an embodiment, the tube is configured to elute a pharmaceutical product.

In an embodiment, the tube is configured to elute an anesthetic.

In an embodiment, the tube is configured to elute a pharmaceutical product selected from the group consisting of: an anti-inflammatory agent, and an antibiotic.

In an embodiment, the tube is flexible.

In an embodiment, the tube includes a plug, disposed at a proximal end of the tube.

In an embodiment, the apparatus includes a syringe and a syringe needle, which are configured to pierce the plug and inflate the balloon via the tube, and the plug is configured to seal itself subsequent to withdrawal of the syringe.

In an embodiment, the tube is configured to be passed into the patient's vagina during a medical procedure, and the balloon is configured to be removed from the patient during the same medical procedure.

In an embodiment, at least a portion of the balloon allows light to pass therethrough, and the apparatus includes a scope configured to permit visualization, through the portion of the balloon, of tissue beyond the balloon.

In an embodiment, the apparatus includes an endpoint indicator, configured to generate a signal indicative of a desired endpoint of the occluding of the uterine artery.

In an embodiment, the endpoint indicator includes a temperature sensor, suitable for measuring a temperature of the fibroid.

In an embodiment, the endpoint indicator includes a timer.

In an embodiment, the balloon is configured to deflate in response to the signal generated by the endpoint indicator.

In an embodiment, the apparatus is configured such that the tube can be separated from the balloon and removed from the patient while the balloon remains, inflated, within the patient.

In an embodiment, the balloon includes a valve, through which the tube inflates the balloon, and which inhibits deflation of the balloon after separation of the balloon from the tube.

In an embodiment, the balloon is configured for deflation within the patient following the squeezing, and to reside chronically within the patient.

In an embodiment, the balloon is configured for removal from the patient following the deflation.

In an embodiment, the apparatus includes an extractor, coupled to the balloon, configured to reside in part within the patient's vagina while the balloon is causing the local squeezing, and configured to facilitate extraction of the balloon from the patient.

In an embodiment, the apparatus includes a sensor, configured to generate a signal that is indicative of proximity of the distal tip to the uterine artery.

In an embodiment, the sensor includes an acoustic sensor.

In an embodiment, the sensor includes a pressure sensor.

In an embodiment, the pressure sensor is configured to operate substantially without transmitting energy towards the uterine artery.

In an embodiment, the balloon is shaped to define an orifice that is configured to release contents of the balloon into a body of the patient, when the balloon is within the patient.

In an embodiment, the apparatus includes saline, configured for placement within the balloon and to be at least a portion of the contents of the balloon released into the body of the patient.

In an embodiment, the apparatus includes a pharmaceutical product, configured for placement within the balloon and to be at least a portion of the contents of the balloon released into the body of the patient.

In an embodiment, the pharmaceutical product includes an anesthetic.

In an embodiment, the pharmaceutical product includes a pharmaceutical selected from the group consisting of: an anti-inflammatory agent, and an antibiotic.

In an embodiment, the balloon and orifice are configured such that the release of the contents occurs over a time period that lasts for at least 30 minutes.

In an embodiment, the time period is at least 3 hours, and the balloon and orifice are configured such that the release of the contents occurs over the time period that lasts at least 3 hours.

In an embodiment, the balloon and orifice are configured such that the release of the contents reduces a volume of the balloon at an average rate of between 1%/hour and 30%/hour, calculated over a 30 minute period.

In an embodiment, the balloon and orifice are configured such that the average rate is between 1%/hour and 5%/hour.

In an embodiment, the balloon and orifice are configured such that the average rate is between 5%/hour and 15%/hour.

In an embodiment, the balloon and orifice are configured such that the average rate is between 15%/hour and 30%/hour.

In an embodiment, the balloon is configured to remain within the patient for at least 7 days following termination of the occlusion.

In an embodiment, at least a portion of the balloon is biodegradable.

In an embodiment, at least a portion of the balloon is not biodegradable.

In an embodiment, the balloon is configured to deflate, without active human intervention, while within the patient.

In an embodiment, the balloon includes a biodegradable deflation element, configured such that degrading of the biodegradable deflation element causes the deflation of the balloon.

In an embodiment, the balloon is configured to deflate at a time that is at least 1 hour after inflation of the balloon.

In an embodiment, the apparatus includes:
an inflation sensor, configured to generate a signal indicative of a level of inflation of the balloon; and
an indicator, configured to generate an indication to a human of the level of inflation.

In an embodiment, the inflation sensor includes a pressure sensor, configured to generate the signal in response to a level of pressure in the balloon.

In an embodiment, the inflation sensor includes a sensor configured to generate the signal in response to a characteristic of blood flow in the uterine artery.

In an embodiment:
the inflation sensor is configured to be attached to the balloon, and
the indicator is configured to be disposed outside of a body of the patient and to receive the signal wirelessly from the inflation sensor.

In an embodiment, the balloon includes an active deflation element, configured to actively cause the deflation of the balloon.

In an embodiment, the active deflation element includes at least one element selected from the group consisting of: a puncturing element, and a heating element.

In an embodiment, the apparatus includes an endpoint indicator, configured to generate a signal indicative of a desired endpoint of the occluding of the uterine artery, and the active deflation element is configured to cause the deflation of the balloon in response to the signal.

In an embodiment, the active deflation element is configured to cause the deflation at a designated time after the occluding of the uterine artery.

In an embodiment, the balloon is configured to deflate at a time that is less than 36 hours after inflation of the balloon.

In an embodiment, the balloon is configured to deflate at a time that is at least 1 hour after inflation of the balloon.

In an embodiment, the balloon is configured to deflate at a time that is between 5 hours and 20 hours after inflation of the balloon.

There is further provided, in accordance with an embodiment of the present invention, a method including:
advancing a tool to a site within a patient, outside of a vagina of the patient and outside of a uterine artery of the patient, but in a vicinity of a portion of the uterine artery that supplies a uterine fibroid; and
squeezing the portion of the uterine artery with the tool, to an extent sufficient to occlude the uterine artery.

In an embodiment, advancing the tool to the site in the vicinity of the portion of the uterine artery includes advancing the tool to within a distance of 4 cm of the portion of the uterine artery.

In an embodiment, the tool includes a tube and a balloon coupled to the tube, and squeezing the portion of the uterine artery includes inflating the balloon.

In an embodiment, the balloon includes a toroidal balloon wrapped around the tube, and squeezing the portion of the uterine artery includes inflating the toroidal balloon.

In an embodiment, the method includes leaving the tube coupled to the balloon throughout the time that the balloon is inflated.

In an embodiment, the tube is flexible, and leaving the tube coupled to the balloon includes leaving the flexible tube coupled to the balloon.

In an embodiment, inflating the balloon includes piercing a self-sealing element at a proximal end of the tube, and inflating the balloon via the tube.

In an embodiment, advancing the tool to the site includes:
advancing a distal end of an introducer to the site; and
advancing a distal end of the tube to the site, via the introducer, the balloon being disposed at the distal end of the tube.

In an embodiment, the introducer includes a metal introducer and advancing the distal end of the introducer includes advancing a distal end of the metal introducer.

In an embodiment, the method includes administering a pharmaceutical product to the patient via the introducer.

In an embodiment, administering the pharmaceutical product to the patient includes administering an anesthetic into the patient.

In an embodiment, administering the pharmaceutical product to the patient includes administering to the patient a pharmaceutical product selected from the group consisting of: an anti-inflammatory agent, and an antibiotic.

In an embodiment, the method includes leaving the tube coupled to the balloon throughout the time that the balloon is inflated.

In an embodiment, the method includes removing the introducer from the patient when the distal tip of the tube is disposed at the site.

In an embodiment, removing the introducer includes splitting the introducer.

In an embodiment, the method includes administering a pharmaceutical product to the patient via the tube.

In an embodiment, administering the pharmaceutical product includes administering an anesthetic.

In an embodiment, administering the pharmaceutical product includes administering a pharmaceutical product selected from the group consisting of: an anti-inflammatory agent, and an antibiotic.

In an embodiment, the tube is flexible, and leaving the tube coupled to the balloon includes leaving the flexible tube coupled to the balloon.

In an embodiment, inflating the balloon includes piercing a self-sealing element at a proximal end of the tube, and inflating the balloon via the tube.

In an embodiment, the method does not include performing lumbar puncture.

In an embodiment, the method includes identifying attainment of a desired endpoint of the occluding of the uterine artery.

In an embodiment, the method includes measuring a temperature of the fibroid, and identifying includes identifying the attainment of the desired endpoint in response to the measured temperature.

In an embodiment, identifying the attainment of the desired endpoint includes comparing an actual duration of occlusion of the uterine artery to a desired duration of occlusion of the uterine artery.

In an embodiment, the method includes terminating the squeezing in response to the identifying.

In an embodiment, terminating includes withdrawing the tool from the patient.

In an embodiment, the method includes, subsequently to the terminating, maintaining at least a portion of the tool within the patient for at least 7 days.

In an embodiment, the method includes terminating the squeezing, without active human intervention, while the tool is within the patient.

In an embodiment, terminating the squeezing includes terminating the squeezing in response to biodegrading of a biodegradable deflation element.

In an embodiment, terminating the squeezing includes terminating the squeezing at a time that is at least 1 hour after an initiating of the squeezing.

In an embodiment, the method includes:
sensing an indication of whether the squeezing has terminated; and
outputting a signal to a human in response to the sensing.

In an embodiment, sensing includes sensing a pressure.

In an embodiment, sensing includes sensing a characteristic of blood flow in the uterine artery.

In an embodiment, the method includes removing the tool from the patient in response to an indication by the outputted signal that the squeezing has terminated.

In an embodiment, the method includes assessing a duration during which the portion of the uterine artery was occluded, and squeezing the portion of the uterine artery again if the assessed duration is determined to be too short.

In an embodiment, the method includes discharging the patient from a healthcare facility at least in part in response to an indication by the outputted signal that the squeezing has terminated.

In an embodiment, terminating the squeezing includes actuating an active element to cause the squeezing to terminate.

In an embodiment, the method includes sensing attainment of a desired endpoint of the occluding of the uterine artery, and actuating the active element includes actuating the active element in response to the sensing.

In an embodiment, actuating the active element includes at least one action selected from the group consisting of: puncturing the tool, and heating the tool.

In an embodiment, actuating the active element includes actuating the active element at a designated time after the occluding of the uterine artery.

In an embodiment, terminating the squeezing includes terminating the squeezing at a time that is less than 36 hours after an initiating of the squeezing.

In an embodiment, terminating the squeezing includes terminating the squeezing at a time that is at least 1 hour after an initiating of the squeezing.

In an embodiment, terminating the squeezing includes terminating the squeezing at a time that is between 5 hours and 20 hours after an initiating of the squeezing.

In an embodiment, the method includes terminating the squeezing of the portion of the uterine artery at a termination time, and leaving at least a portion of the tool within the patient for at least 7 days following the termination time.

In an embodiment, the portion of the tool includes a balloon, and leaving includes leaving the balloon within the patient.

In an embodiment, at least a portion of the balloon is biodegradable, and leaving the balloon includes leaving the balloon to biodegrade within the patient.

In an embodiment, at least a portion of the balloon is not biodegradable, and leaving the balloon includes leaving the balloon to reside permanently within the patient.

In an embodiment, the tool includes a balloon, and squeezing the portion of the uterine includes inflating the balloon.

In an embodiment, at least a portion of the balloon allows light to pass therethrough, and the method includes visualizing, through the portion of the balloon, tissue beyond the balloon.

In an embodiment, the method includes sensing an indication of proximity of the tool to the uterine artery.

In an embodiment, sensing includes acoustically sensing.

In an embodiment, sensing includes sensing a pressure.

In an embodiment, sensing the pressure includes sensing the pressure substantially without transmitting energy towards the uterine artery.

In an embodiment, the method includes releasing contents of the tool into a body of the patient, when the tool is within the patient.

In an embodiment, releasing the contents includes releasing a liquid.

In an embodiment, releasing the liquid includes releasing saline.

In an embodiment, releasing the contents includes releasing a pharmaceutical product.

In an embodiment, releasing the pharmaceutical product includes releasing an anesthetic.

In an embodiment, releasing the contents includes releasing the contents over a time period that lasts for at least 30 minutes.

In an embodiment, releasing the contents includes releasing the contents over a time period that lasts for at least 3 hours.

In an embodiment, releasing the contents includes reducing a volume of the tool at an average rate of between 1%/hour and 30%/hour, calculated over a 30 minute period.

In an embodiment, reducing the volume includes setting the average rate to between 1%/hour and 5%/hour.

In an embodiment, reducing the volume includes setting the average rate to between 5%/hour and 15%/hour.

In an embodiment, reducing the volume includes setting the average rate to between 15%/hour and 30%/hour.

There is also provided, in accordance with an embodiment of the invention, apparatus including:

a tube, configured to be passed into a patient's vagina and to penetrate vaginal tissue until a distal tip of the tube is outside of a uterine artery of the patient, but in a vicinity of a portion of the uterine artery that supplies a uterine fibroid; and a tool, configured to be disposed at the distal tip and to cause local squeezing of the portion of the uterine artery to an extent sufficient to occlude the uterine artery.

There is yet further provided, in accordance with an embodiment of the present invention, apparatus including:

a tube, configured to be passed into a body of a patient until a distal tip of the tube is outside of an artery of the patient; and a balloon, configured to be disposed at the distal tip and to be inflated to cause local squeezing of a portion of the artery to an extent sufficient to occlude the artery.

There is still further provided, in accordance with an embodiment of the present invention, a method including:

advancing a balloon to a site within a patient, outside of an artery of the patient; and squeezing the artery by inflating the balloon to an extent sufficient to occlude the artery.

There is additionally provided, in accordance with an embodiment of the present invention, a method including:

surgically implanting a balloon within a patient; and configuring the balloon to deflate, without human intervention, within 36 hours.

There is also provided, in accordance with an embodiment of the invention, a method including:

surgically implanting a balloon within a patient, via a vagina of the patient; and configuring the balloon to deflate without human intervention.

There is yet further provided, in accordance with an embodiment of the present invention, a method including:

placing a balloon and a sensor within a patient, via a vagina of the patient; and receiving from the sensor an indication of a state of inflation of the balloon.

There is still further provided, in accordance with an embodiment of the present invention, a method including:

placing a balloon and a sensor within a patient;

initiating a medical procedure by inflating the balloon; and receiving from the sensor an indication that the procedure has been completed.

There is additionally provided, in accordance with an embodiment of the present invention, a method including:

placing a balloon within a patient; and configuring the balloon to deflate without human intervention.

There is also provided, in accordance with an embodiment of the invention, a method including:

implanting a biodegradable balloon within a patient; and initiating a medical procedure by inflating the balloon.

The present invention will be more fully understood from the following detailed description of embodiments thereof, taken together with the drawings, in which:

BRIEF DESCRIPTION OF THE DRAWINGS

FIGS. 4-6 are schematic illustrations of apparatus for treating uterine fibroids, in accordance with another embodiment of the present invention;

FIGS. 7A-C are schematic illustrations of a procedure for placing a portion of the apparatus of FIGS. 4-6, in accordance with an embodiment of the present invention;

FIGS. 11A-C are schematic illustrations of a procedure for placing a portion of the apparatus of FIGS. 8-10, in accordance with an embodiment of the present invention;

FIGS. 12A and 12B are schematic illustrations of apparatus for delivering contents of a balloon, in accordance with an embodiment of the present invention;

FIGS. 14A-D are schematic illustrations of apparatus for treating fibroids, in accordance with another embodiment of the present invention; and FIG. 15 is a schematic illustration of a toroidal balloon for treating fibroids, in accordance with an embodiment of the present invention.

DETAILED DESCRIPTION OF EMBODIMENTS

Figure 1:
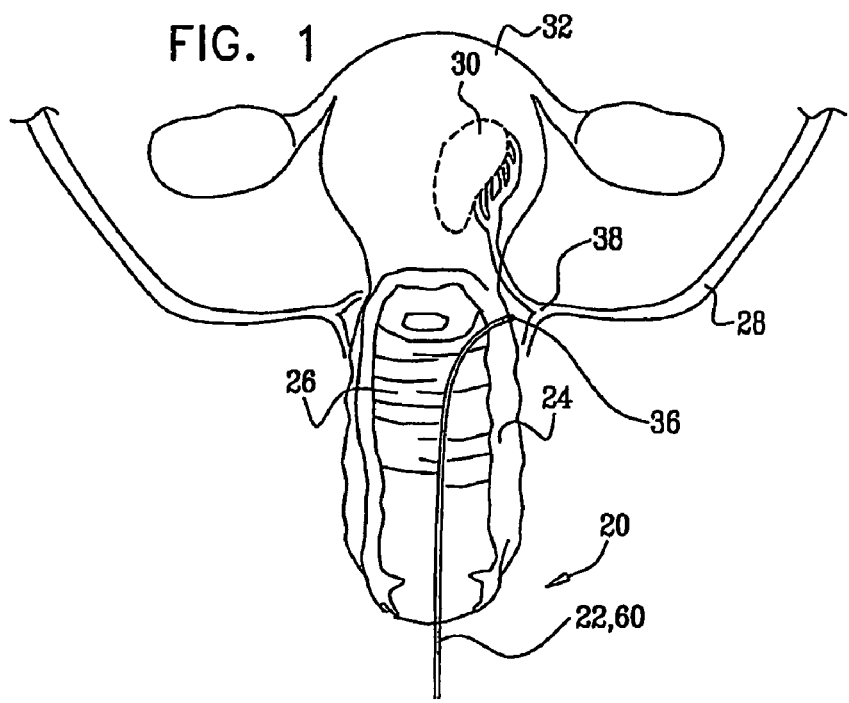
FIGS. 1 and 2 are schematic illustrations of a method and apparatus for treating uterine fibroids, in accordance with an embodiment of the present invention.
Figure 2:
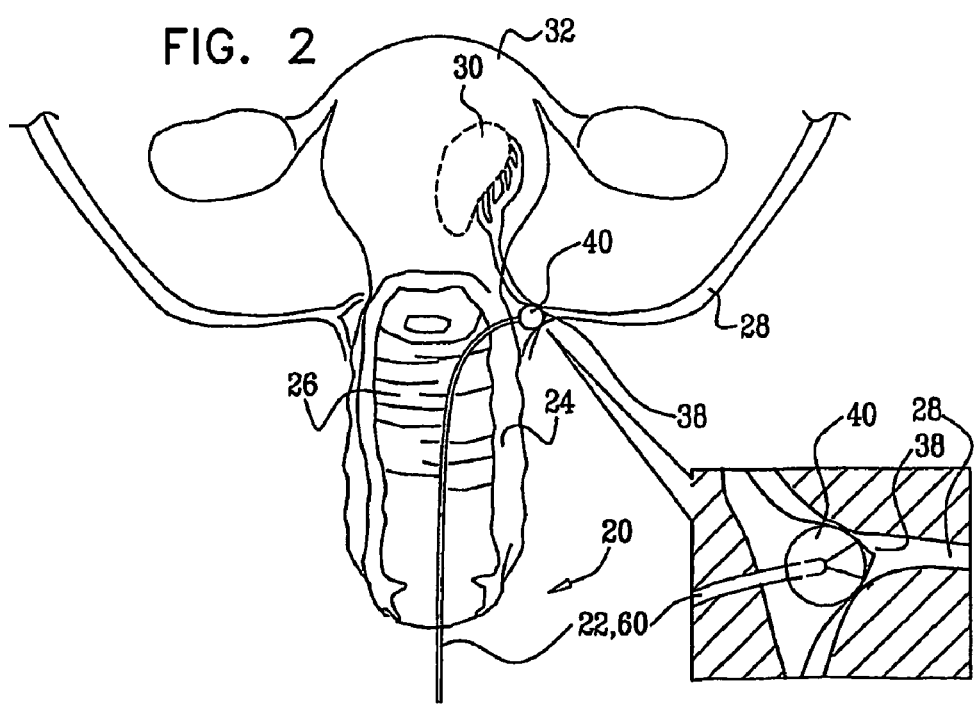

FIGS. 1 and 2 are schematic illustrations of apparatus 20 for treating a fibroid 30 in a uterus 32 of a patient, in accordance with an embodiment of the present invention. Fibroid 30 receives oxygenated blood from a uterine artery 28. Apparatus 20 occludes (i.e., occludes completely, or occludes at least in part) uterine artery 28 with a tool that compresses the artery from a site within the patient's body, outside of the patient's vagina 26 and outside of the artery.

In some embodiments of the present invention, apparatus 20 comprises a tool such as a tube 22, configured to be passed into the patient's vagina 26. (Tube 22 may be disposed within another tool, such as a longitudinal carrier 60 shown in detail in FIGS. 3A and 3B.) Tube 22 penetrates vaginal tissue 24 until a distal tip 36 of the tube is outside of uterine artery 28, but in a vicinity of a portion 38 of the uterine artery that supplies fibroid 30. A balloon 40 (FIG. 2) is configured to be disposed at distal tip 36, and to be inflated to cause local squeezing of portion 38 of uterine artery 28, to an extent sufficient to occlude the uterine artery. In some embodiments, balloon 40 occludes portion 38 of the uterine artery by being inflated at a non-specific site in the vicinity of portion 38, the inflation causing tissue in the vicinity to become compressed. Typically, the balloon is disposed within 4 cm of portion 38 in order to occlude portion 38.

Artery 28 is typically occluded for a sufficient time to partially or completely destroy fibroid 30, while not causing substantial levels of damage to non-tumor tissue of the patient. As appropriate, techniques and apparatus known in the art and/or described in one or more of the references cited in the Background section of the present patent application may be combined with techniques described herein, mutatis mutandis. For example, cutting and/or tissue penetration tools may be used to facilitate passage of distal tip 36 towards portion 38 of uterine artery 28. Similarly, tube 22 may be advanced through a working channel of an endoscope.

Figure 3A:
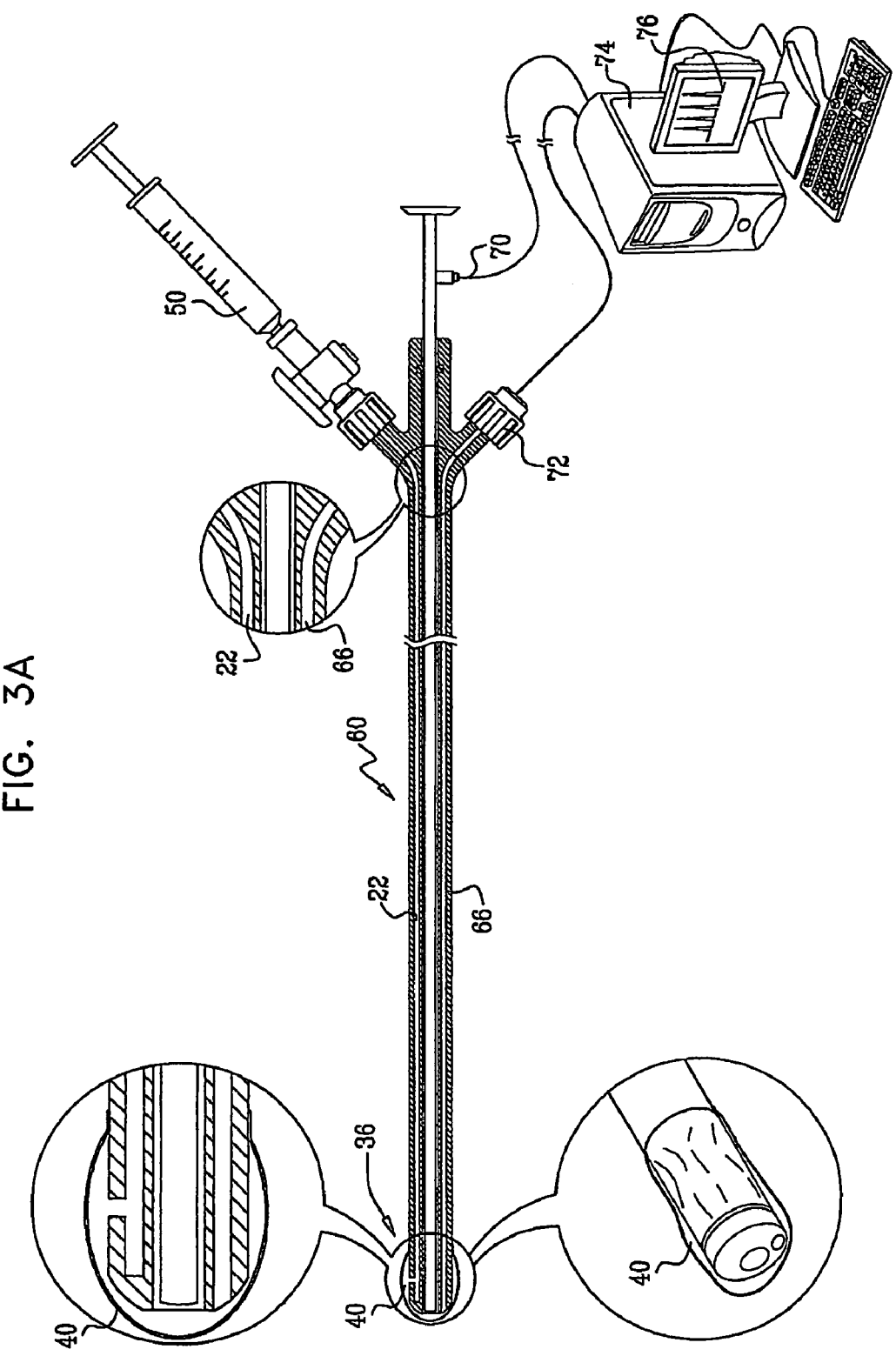
FIGS. 3A and 3B are schematic illustrations showing details of the apparatus of FIG. 1, in accordance with an embodiment of the present invention.

FIG. 3A is a schematic illustration showing details of apparatus 20, in accordance with an embodiment of the present invention. It is to be appreciated that the configuration of hardware components in FIG. 3A is shown by way of illustration and not limitation, and that the scope of the present invention includes other apparatus suitable for carrying out the method described herein.

Apparatus 20 as shown in FIG. 3A comprises a longitudinal carrier 60 having a plurality of channels. One of these channels typically defines tube 22. Typically, carrier 60 comprises an endoscope, which allows visualization of the environment of distal tip 36. For some applications, balloon 40 is transparent, and light entering the endoscope through a light guide 70 illuminates the environment of distal tip 36. Light reflected from the site passes through balloon 40 and assists a physician operating apparatus 20 to determine whether the balloon has arrived at the desired location. In an embodiment, the image obtained through balloon 40 is displayed on a workstation 74 of apparatus 20.

For some applications, apparatus 20 comprises a sensor 72, configured to generate a signal that is indicative of the proximity of distal tip 36 to uterine artery 28. In an embodiment, sensor 72 comprises a pressure sensor in fluid communication with balloon 40 via a channel 66. The proximity of distal tip 36 to uterine artery 28 in this embodiment is typically determined based on the clarity of an arterial pressure trace 76 displayed on workstation 74 and/or the value of a mathematical variable calculated based on the signal. For example, the variable may be based on a fourier transform of the signal, and may represent the percentage of the signal which contains fluctuations near 1 Hz. FIG. 3A show pressure trace 76 clearly varying in a manner characteristic of arterial blood flow, indicating that distal tip 36 is near to but not occluding flow in uterine artery 28.

For some applications, sensor 72 comprises an acoustic sensor, whose output is typically channeled through a loudspeaker (not shown) to allow the physician to assess how close distal tip 36 is to uterine artery 28. In this manner, sensor 72 with channel 66 acts in a manner analogous to a stethoscope.

It is to be appreciated that the position and mechanical and electrical characteristics of sensor 72 are described herein and shown in the figures by way of illustration and not limitation. For some applications, sensor 72 is otherwise configured, for example, by being located at distal tip 36. In any case, because of the close distance of distal tip 36 to uterine artery 28, sensor 72 typically generates the signal indicative of the proximity of distal tip 36 to uterine artery 28 substantially without using the transmission of energy to the artery and the subsequent collection of reflected energy from the artery. Instead, in these embodiments, sensor 72 senses a parameter in a vicinity of the tip which is indicative of the proximity of the tip to the artery. Alternatively, energy transmission (e.g., ultrasound) is used, at least in part, to facilitate the determination of proximity.

Figure 3B:
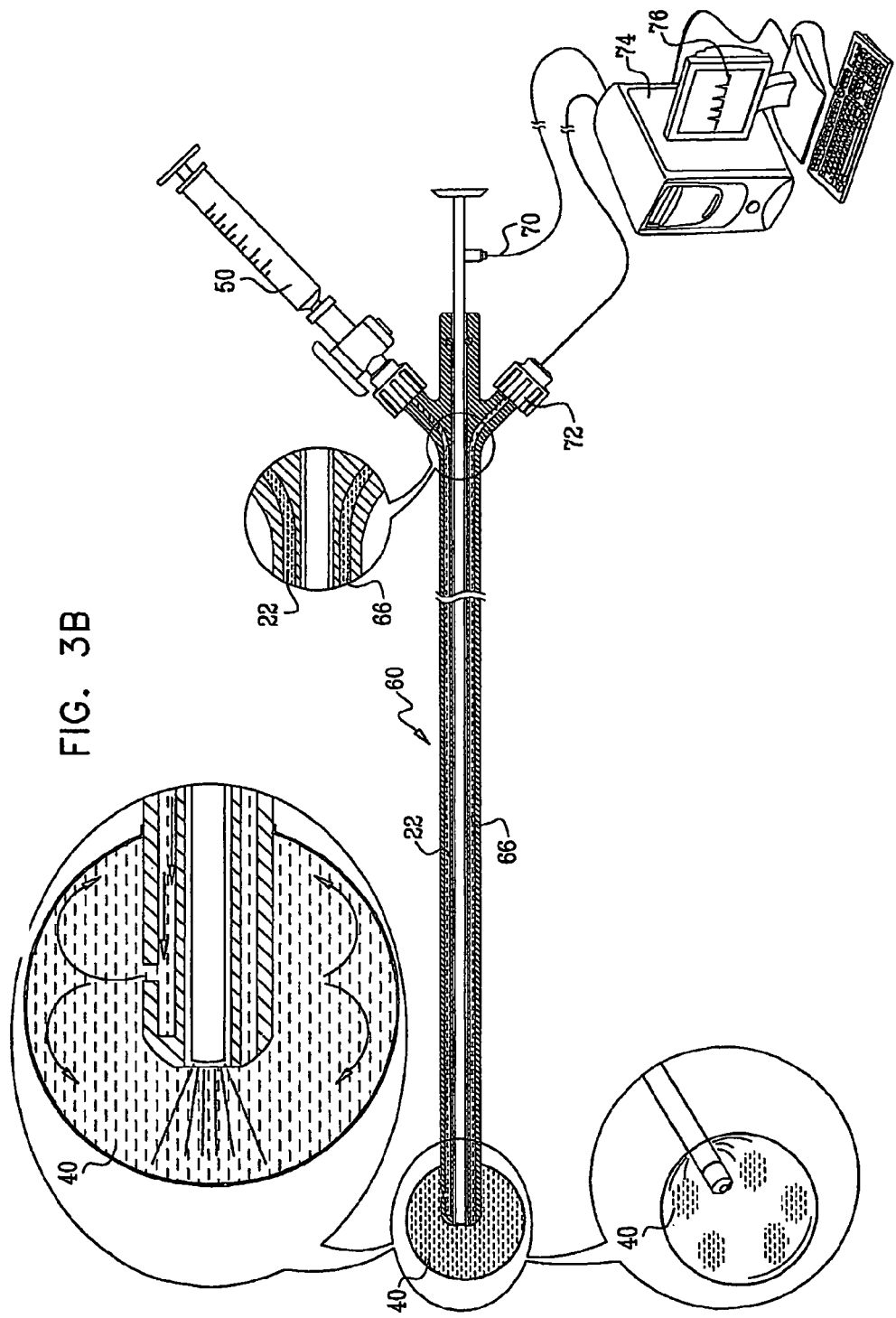

FIG. 3B is a schematic illustration of apparatus 20 during operation thereof, in accordance with an embodiment of the present invention. When it is determined that distal tip 36 is sufficiently near to, or in contact with, uterine artery 28, balloon 40 is inflated by a pressure source 50 of apparatus 20. Typically, but not necessarily, the level of inflation of balloon 40 is increased until the signal from sensor 72 (or another sensor) indicates that artery 28 has been occluded. For example, variations in the signal that are approximately 1 Hz may be heard or seen to decrease substantially when the artery has been occluded. Pressure trace 76 in FIG. 3B is seen to be smaller than in FIG. 3A, indicating that the balloon is at least partially occluding the uterine artery.

Pressure source 50 typically comprises a manual syringe, as shown, but may alternatively comprise an automatic pressure source, e.g., one that is activated by workstation 74. Pressure source 50 typically inflates balloon with a saline solution, another liquid, or a gas. Inflation of balloon 40 compresses portion 38 of uterine artery 28, thereby occluding the artery and depriving fibroid 30 of its blood supply.

Figure 4:
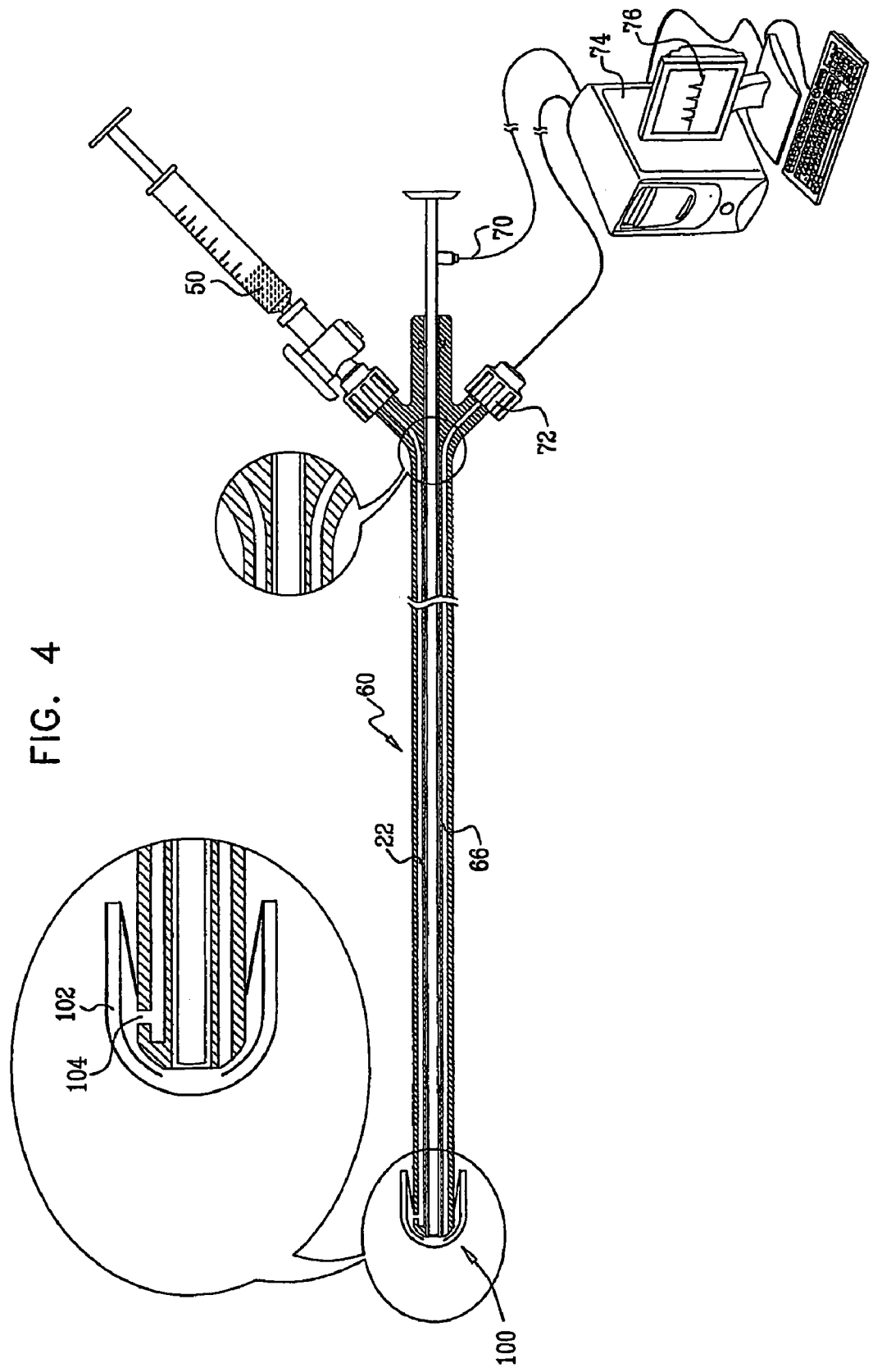

Reference is now made to FIGS. 4-6, which are schematic illustrations of apparatus 100 for treating uterine fibroids, in accordance with another embodiment of the present invention. Apparatus 100 is generally similar to apparatus 20 described with reference to FIGS. 1-3, except as described hereinbelow.

Apparatus 100 comprises a balloon 102 that is disposed at distal tip 36 during initial placement of apparatus 100 (FIG. 4). Balloon 102 is inflated via a balloon port 104 (FIG. 5). Distal tip 36 is separated from balloon 102 by pulling distal tip 36 in a direction 108 away from the balloon (FIG. 6). When distal tip 36 is separated from balloon 102, a valve 106 of the balloon closes, preventing or inhibiting deflation of the balloon.

Reference is now made to FIGS. 7A-C, which are schematic illustrations of a procedure for placing balloon 102 within the patient's body, in accordance with an embodiment of the present invention. The procedure is generally similar to that shown and described with reference to FIGS. 1 and 2, except as noted. Tube 22 penetrates vaginal tissue 24 until apparatus 100 is outside of uterine artery 28, but in a vicinity of portion 38 of the uterine artery (FIG. 7A). Balloon 102 is inflated via tube 22 (FIG. 7B). Tube 22 is withdrawn, leaving balloon 102 inflated and compressing (squeezing) the portion of uterine artery 28 that supplies the fibroid (FIG. 7C).

Figure 8:
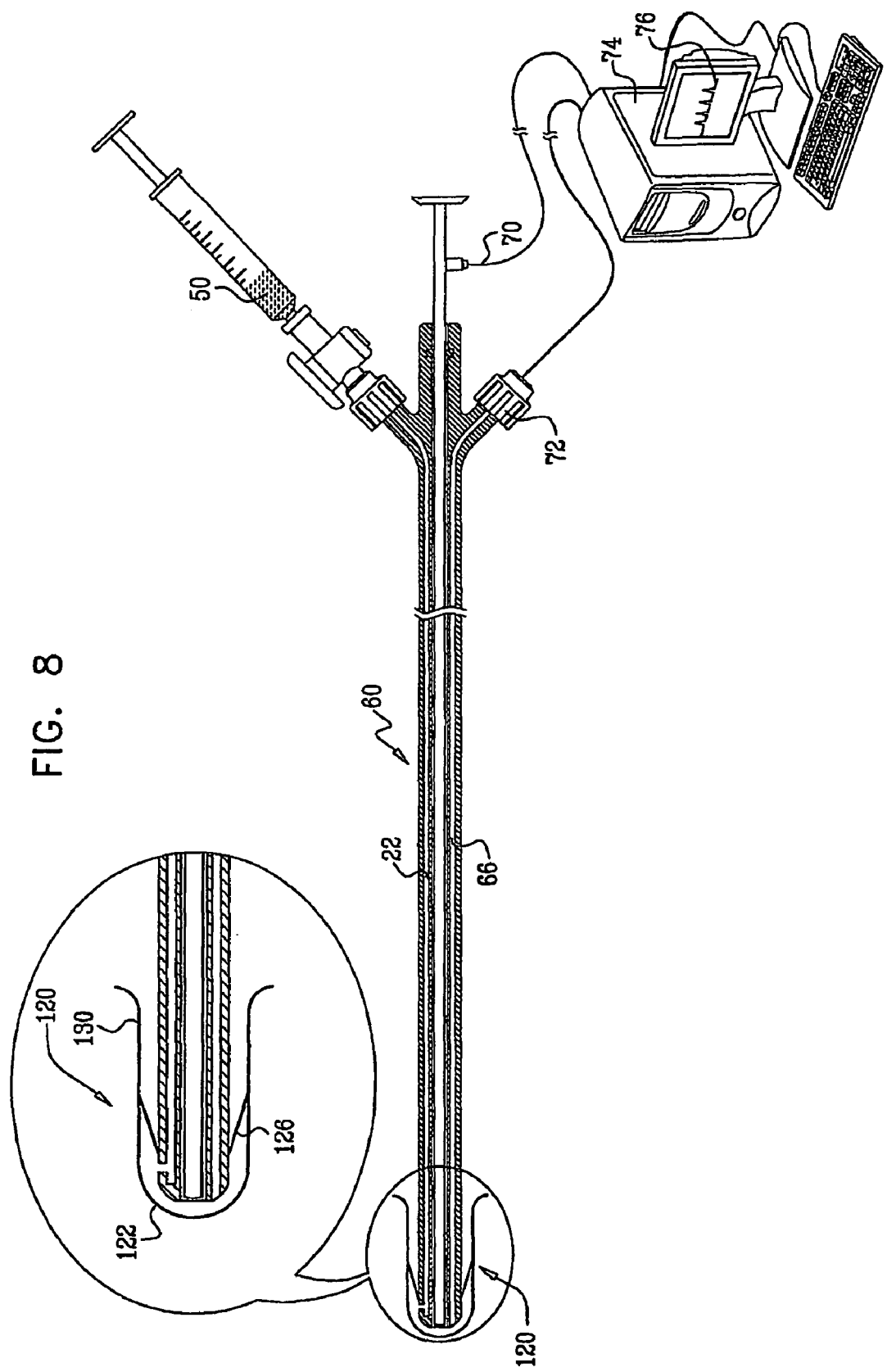
FIGS. 8-10 are schematic illustrations of apparatus for treating uterine fibroids, in accordance with yet another embodiment of the present invention.
Figure 9:
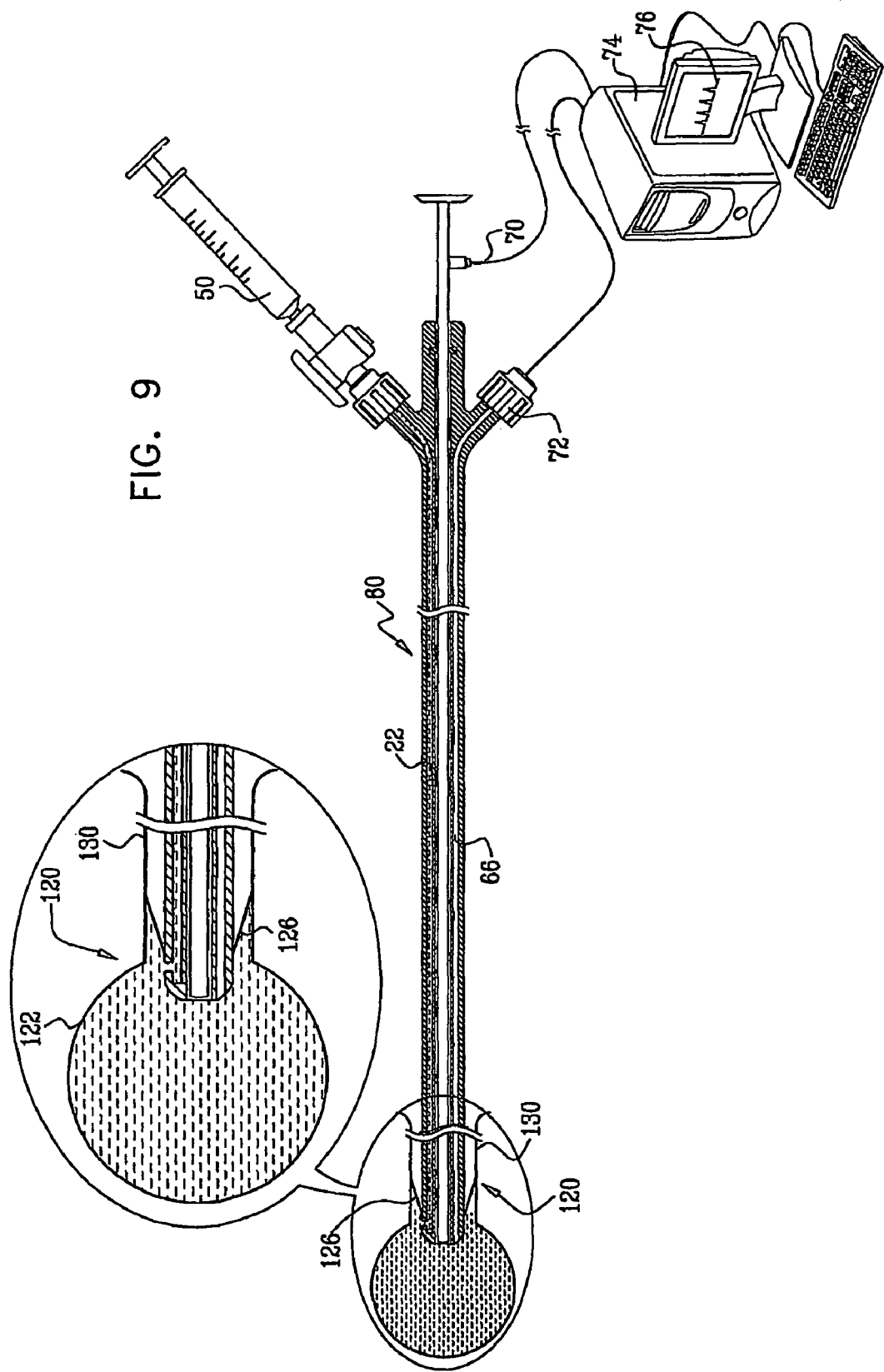
Figure 10:
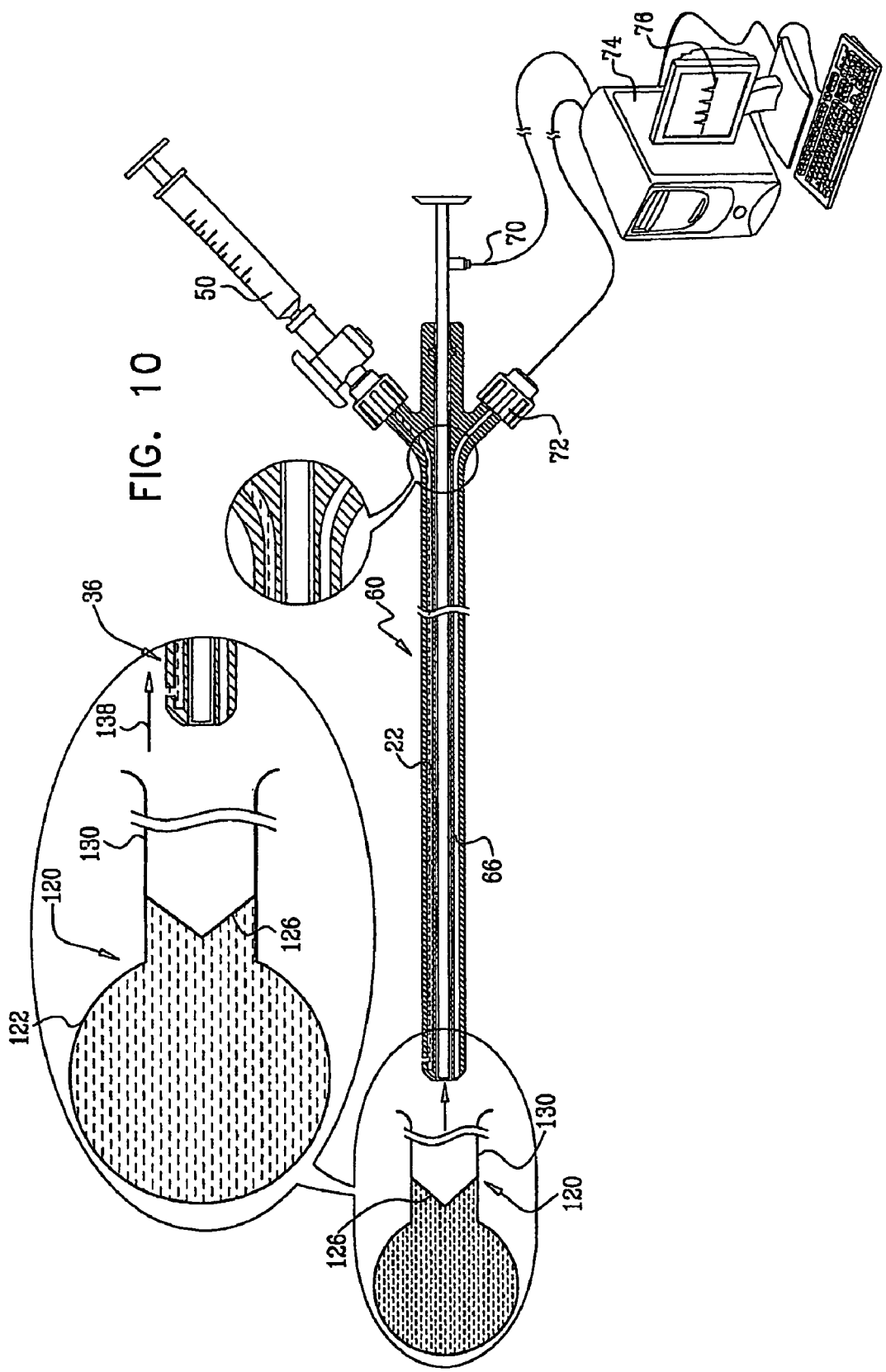

Reference is now made to FIGS. 8-10, which are schematic illustrations of apparatus 120 for treating uterine fibroids, in accordance with an embodiment of the present invention. Apparatus 120 is generally similar to apparatus 100 described with reference to FIGS. 4-6, except as described hereinbelow.

Apparatus 120 comprises a balloon 122 that is disposed at distal tip 36 during initial placement of apparatus 120 (FIG.

8). Balloon 122 is inflated (FIG. 9). Distal tip 36 is separated from balloon 122 by pulling distal tip 36 in a direction 138 away from the balloon (FIG. 10). When distal tip 36 is separated from balloon 122, a valve 126 of the balloon closes, preventing or inhibiting deflation of the balloon.

Figure 11C:
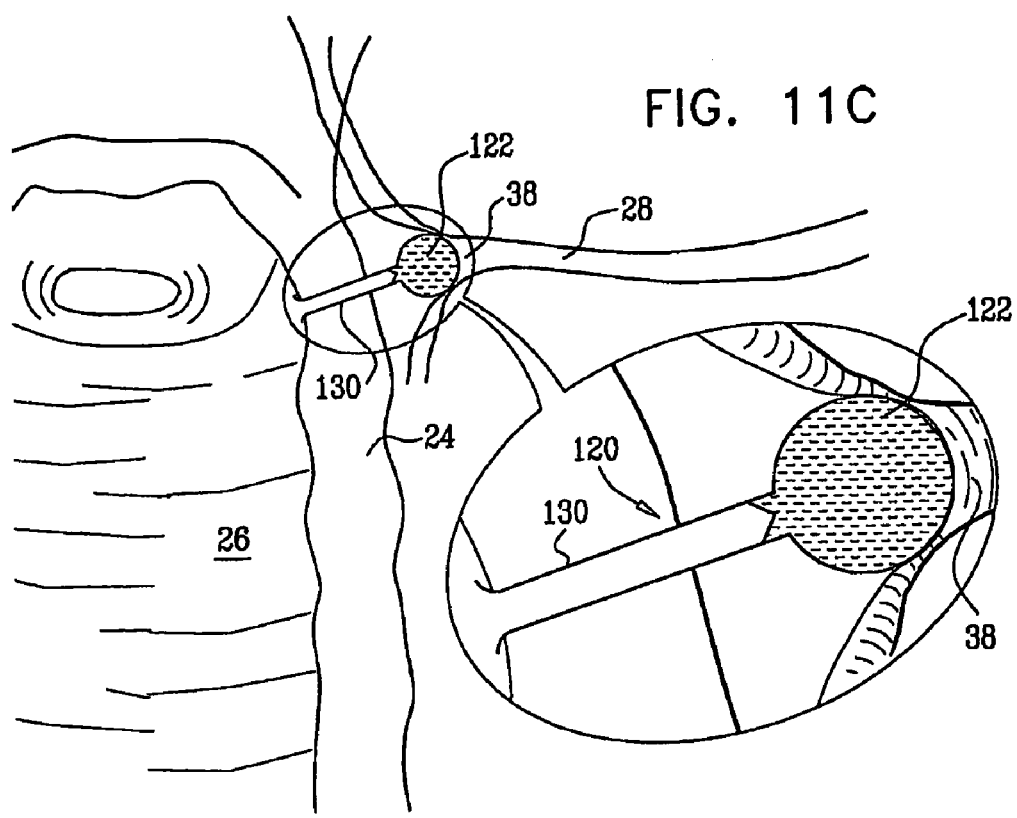

Reference is now made to FIGS. 11A-C, which are schematic illustrations of a procedure for placing balloon 122 within the patient's body, in accordance with an embodiment of the present invention. The procedure is generally similar to that shown and described with reference to FIGS. 7A-C, except as noted. Tube 22 penetrates vaginal tissue 24 until apparatus 120 is outside of uterine artery 28, but in a vicinity of portion 38 of the uterine artery (FIG. 11A). Balloon 122 is inflated via tube 22 (FIG. 11B). Tube 22 is withdrawn, leaving balloon 122 inflated and compressing (squeezing) the portion of uterine artery 28 that supplies the fibroid (FIG. 11C). An extractor 130, coupled to balloon 122, typically resides in part within vagina 26 while balloon 122 is squeezing portion 38 of uterine artery 28. Extractor 130 facilitates extraction of the balloon from the patient when it is determined that occlusion of the uterine artery should terminate.

Reference is now made to FIGS. 12A and 12B, which are schematic illustrations of a system 140 comprising a balloon 142 configured to release at least a portion of its contents 144 while in the patient's body, in accordance with an embodiment of the present invention. As appropriate, balloon 142 may comprise any of balloons 40, 102, or 122, described hereinabove, mutatis mutandis, and may be configured for use in place of these balloons.

In an embodiment, an orifice 148 of balloon 142 slowly releases contents 144 in order to generate a slow deflation of the balloon, e.g., over at least 30 minutes, such as at least 3 hours or at least 10 hours. The rate of release is typically configured such that a volume of balloon 142 decreases at an average rate of between 1%/hour and 30%/hour (e.g., 1%-5%/hour, 5%-15%/hour, or 15%-30%/hour), calculated over a 30 minute period. By way of illustration and not limitation, this use of system 140 is useful when balloon 142 comprises balloon 102, described hereinabove with reference to FIGS. 4-7. In particular, balloon 142 when it comprises balloon 102 is typically configured to remain in the patient's body chronically or to biodegrade. The releasing of contents 144 causes a desired slow deflation of the balloon at generally the time when occlusion of the uterine artery should terminate. For these purposes, contents 144 typically comprise saline and/or another biocompatible fluid.

Alternatively or additionally, contents 144 comprise a pharmaceutical product, such as an anesthetic (e.g., lidocaine), an antibiotic, and/or an anti-inflammatory agent. Release of contents 144 within the patient's body, in this case, does not necessarily cause a substantial reduction in the volume of balloon 142 (but may be configured to do so nevertheless, for example, when balloon 142 comprises balloon 102).

It is noted that volume reduction by release of contents 144 through orifice 148 is suitable for any of the balloons described herein.

In an embodiment, contents 144 are released passively, due to pressure within balloon 142. Alternatively or additionally, the contents are released actively, e.g., due to a pump. For some applications, the pump comprises an expanding gas generated, for example, by a combination of chemicals or by hydrolysis. The expanding gas expels contents 144 at a desired rate, using techniques that are known in the art.

Figure 13A:
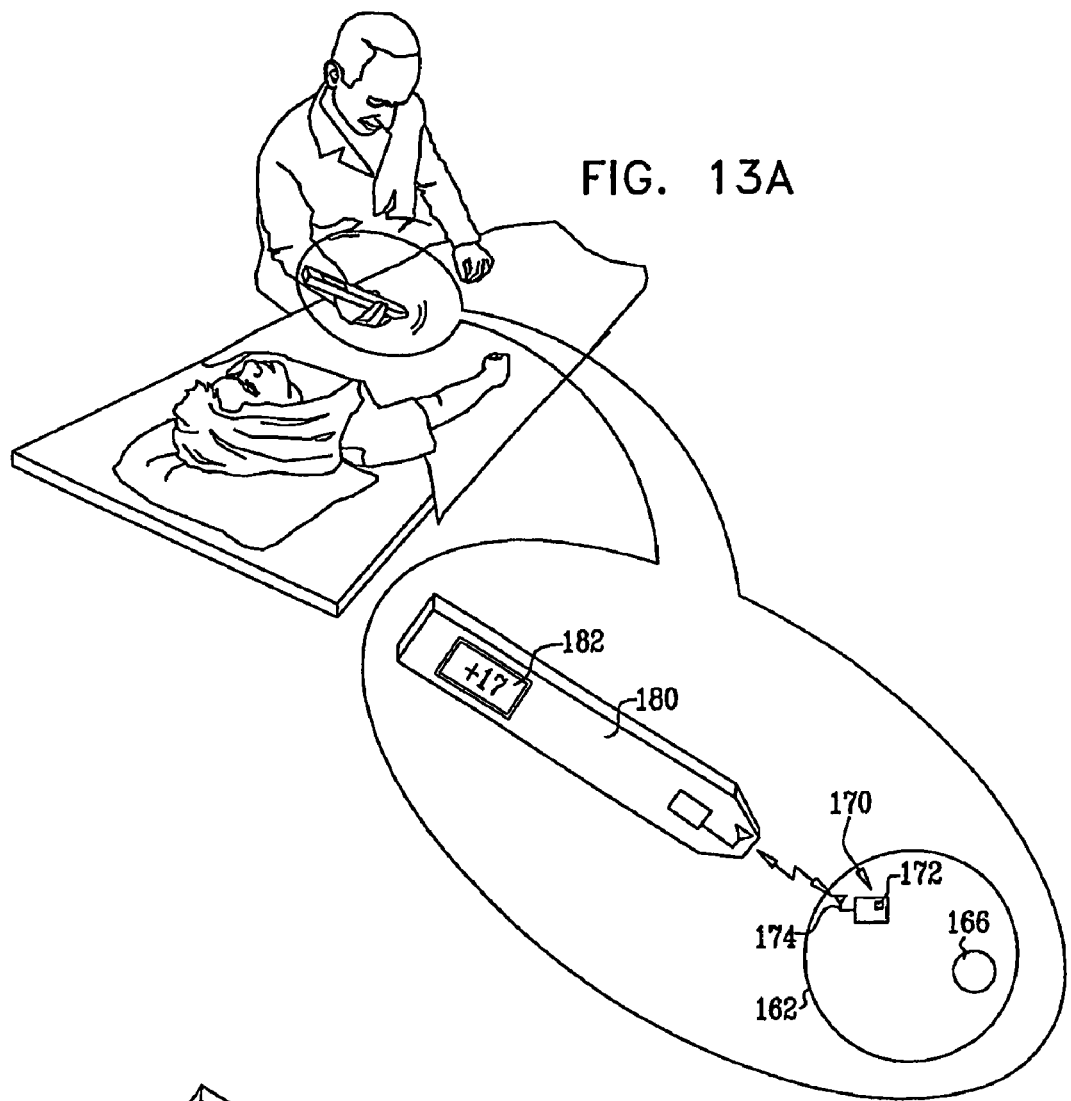
FIGS. 13A and 13B are schematic illustrations of apparatus for deflating a balloon, in accordance with an embodiment of the present invention.
Figure 13B:
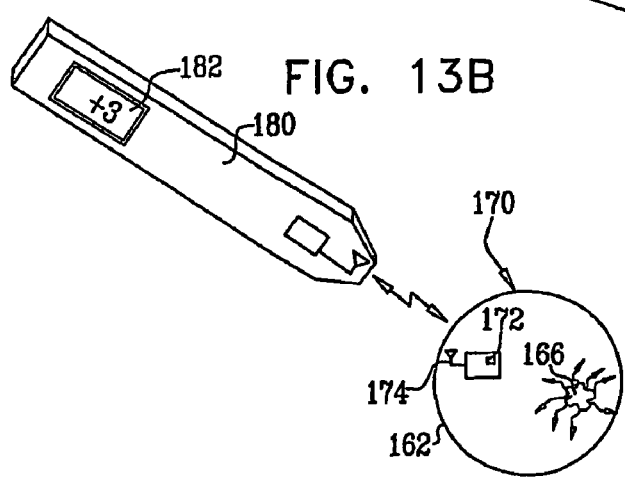

Reference is now made to FIGS. 13A and 13B, which are schematic illustrations of apparatus for deflating a balloon 162, in accordance with an embodiment of the present invention. As appropriate, balloon 162 may comprise any of balloons 40, 102, 122, or 142 described hereinabove, mutatis mutandis, and may be configured for use in place of these balloons.

Balloon 162 is typically configured to deflate, without active human intervention, while within the patient. In an embodiment, balloon 162 comprises a deflation element 166 that operates passively. For example, deflation element 166 may be biodegradable (FIG. 13A), and the balloon configured such that degrading of deflation element 166 causes the deflation of the balloon (FIG. 13B). Typically, deflation element 166 is configured to degrade sufficiently to cause the deflation of balloon 162 between about 1 and 36 hours after placement within the patient, e.g., between about 5 and 10 hours thereafter.

In an embodiment, deflation element 166 is configured to actively cause the deflation of balloon 162. For example, deflation element 166 may comprise a puncturing element or a heating element, which is actuated at an appropriate time to cause deflation of the balloon by puncturing or heating. The deflation element in this case may operate automatically (i.e., without human intervention), or in response to a command received from a human operator.

For some applications, an endpoint indicator is provided, which is configured to generate an endpoint signal indicative of a desired endpoint of the occluding of the uterine artery. Deflation element 166 typically deflates balloon 162 in response to the signal. In an embodiment, the endpoint indicator senses a temperature of fibroid 30, and generates the endpoint signal when the temperature of the fibroid equilibrates to the temperature of surrounding tissue. (In many patients, a fibroid is slightly warmer than surrounding tissue.) Alternatively, the endpoint signal continuously indicates the temperature of the fibroid, and a human interprets the endpoint signal to determine whether the desired endpoint has been reached. In an embodiment, the endpoint indicator comprises a timer, and the endpoint signal corresponds to a desired duration for occlusion of uterine artery 28 (e.g., a duration that is between about 1 and 36 hours, such as about 5-10 hours). In this case, deflation element 166 typically causes the deflation of balloon 162 at the end of this time period, either automatically or in response to a command.

In an embodiment, an inflation sensor 170 is configured to generate a signal indicative of a level of inflation of balloon 162. Inflation sensor 170 is typically attached to the balloon (as shown), but may alternatively be disposed remotely from the balloon. An indicator 182 is typically provided to generate an indication to a human of the level of inflation. The indication is typically numerical (as shown), but may alternatively or additionally be, for example, textual or color coded (e.g., red=fully inflated; yellow=partially inflated; and green=approximately deflated). Indicator 182 is typically configured to be disposed outside of the patient's body, e.g., on a wand 180, and to receive the signal wirelessly from the inflation sensor.

When inflation sensor 170 indicates that balloon 162 has deflated, the balloon is typically removed or allowed to remain chronically, and the patient examined and discharged from the healthcare facility (e.g., a hospital or doctor's office).

In an embodiment, inflation sensor 170 comprises a pressure sensor 172, configured to generate the signal in response to a level of pressure in the balloon. Alternatively, inflation sensor 170 comprises another device configured to detect a property of the balloon indicative of the inflation thereof, such as a strain gauge coupled to the balloon. For some applications, the inflation sensor is configured to generate the signal in response to a characteristic of blood flow in uterine artery 28. For example, the inflation sensor may comprise an ultrasound sensor or a pressure sensor. Restoration of pulsatile flow in uterine artery 28 (following its reduction during uterine artery occlusion) is typically interpreted as indicating that balloon 162 has deflated. If the restoration of pulsatile flow is detected prematurely (e.g., less than a predetermined time, such as 1 hour or 6 hours following initiation of uterine artery occlusion), then the flow restoration is typically interpreted to indicate that the balloon has prematurely deflated or moved out of proper positioning with respect to uterine artery 28. In this case, appropriate steps are taken to re-occlude the uterine artery.

Inflation sensor 170 is typically battery operated, but may alternatively receive power via an antenna 174, ultrasound transducer, or other suitable circuitry known in the art.

Reference is now made to FIGS. 14A-D, which are schematic illustrations of apparatus 200 for treating uterine fibroids, in accordance with another embodiment of the present invention. Apparatus 200 is, generally similar to apparatus 20 described with reference to FIGS. 1-3, except as described hereinbelow.

Figure 14A:
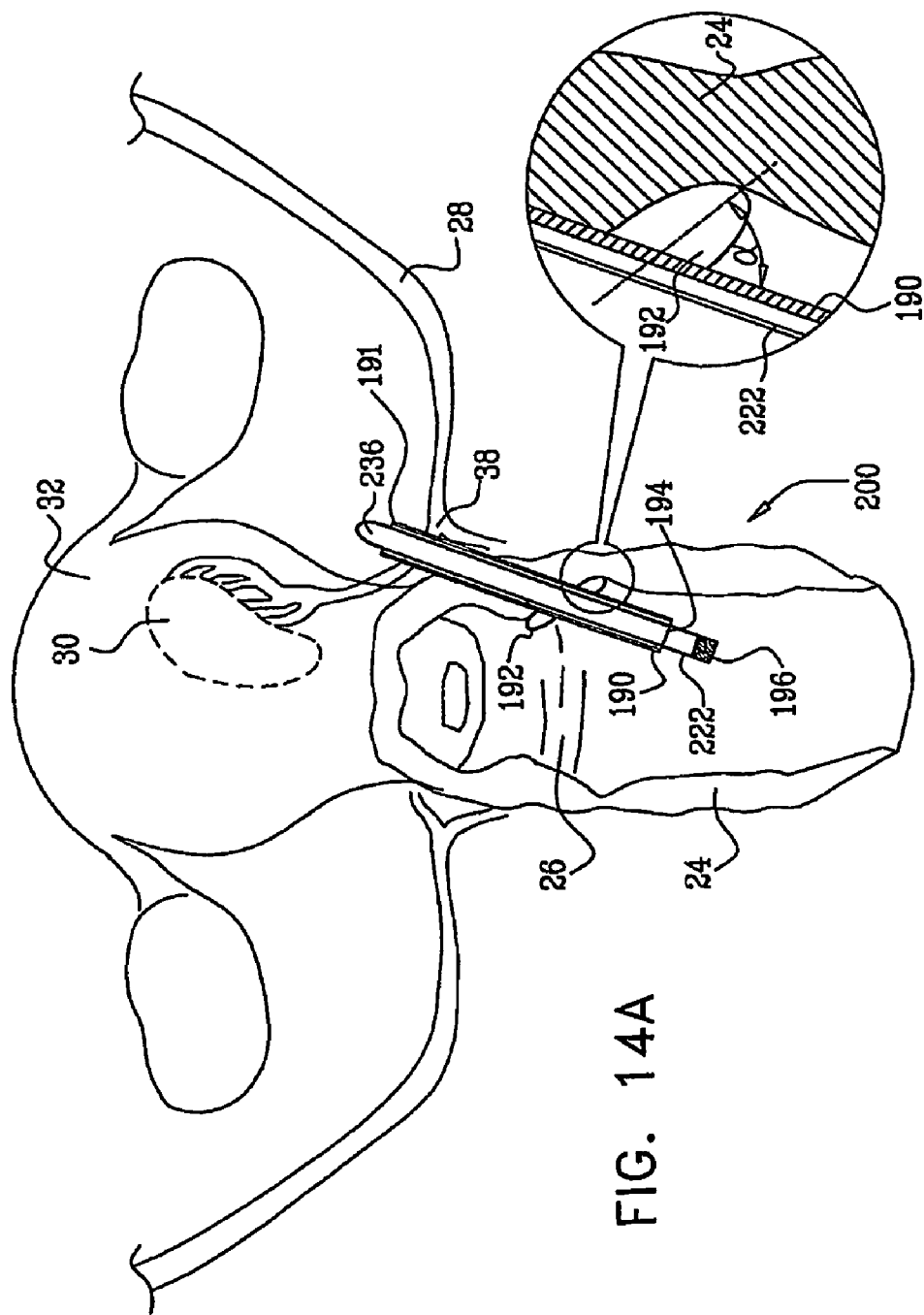

Apparatus 200 comprises an introducer 190 configured to penetrate vaginal tissue 24. The introducer, which is typically cylindrical, comprises a stopper 192 disposed around the outside of the introducer. The stopper is disposed such that it stops the advancement of the introducer through the vaginal tissue when a distal tip 191 of the introducer is disposed in the vicinity of portion 38 of the uterine artery that supplies fibroid 30. A tube 222 is passed through the introducer until a distal tip 236 of the tube is in the vicinity of portion 38. Typically, tube 222 comprises a marker 194, the marker being disposed such that when the distal tip of the tube is in the vicinity of portion 38, the marker is adjacent to the proximal end of the introducer. The marker thus acts as a guide, showing how far to advance tube 222 through introducer 190. FIG. 14A shows apparatus 200 at this stage, tube 222 having been passed through introducer 190 until the marker is adjacent to the proximal end of the introducer.

For some applications, a pharmaceutical-administration tube (not shown) within introducer 190 is configured to facilitate the administration of a pharmaceutical, for example, an anesthetic, an anti-inflammatory agent, and/or an antibiotic, to the patient. For example, a syringe may inject the pharmaceutical into the patient, via the pharmaceutical-administration tube.

In some embodiments, introducer 190 is splittable. Subsequent to tube 222 passing through the introducer, the introducer is split and removed from the vagina.

Figure 14B:
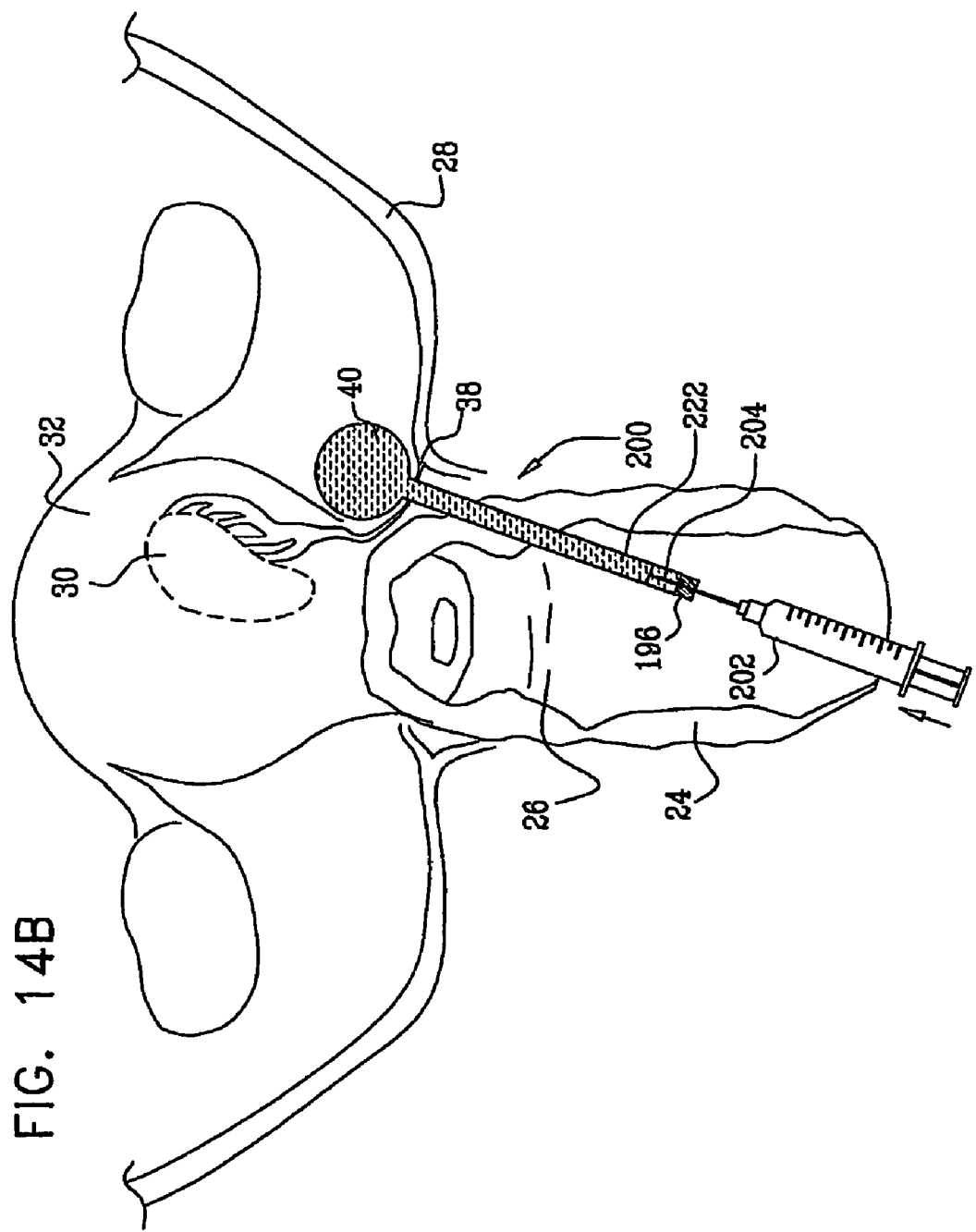

In some embodiments, tube 222 comprises a self-sealing plug 196 at its proximal end. Balloon 40 is disposed at distal tip 236 of the tube. When the distal tip of the tube is in the vicinity of portion 38 and introducer 190 has been removed from the vagina, the balloon is inflated, typically using a syringe 202. Typically, a syringe needle 204 pierces plug 196, and liquid is injected through tube 222 into balloon 40. FIG. 14B shows the syringe inflating the balloon by injecting a liquid into tube 222. Having inflated the balloon, the syringe is withdrawn, plug 196 seals itself, and the balloon remains in an inflated state. The balloon compresses tissue in the vicinity of portion 38 of uterine artery 28, causing portion 38 to become occluded.

Figure 14C:
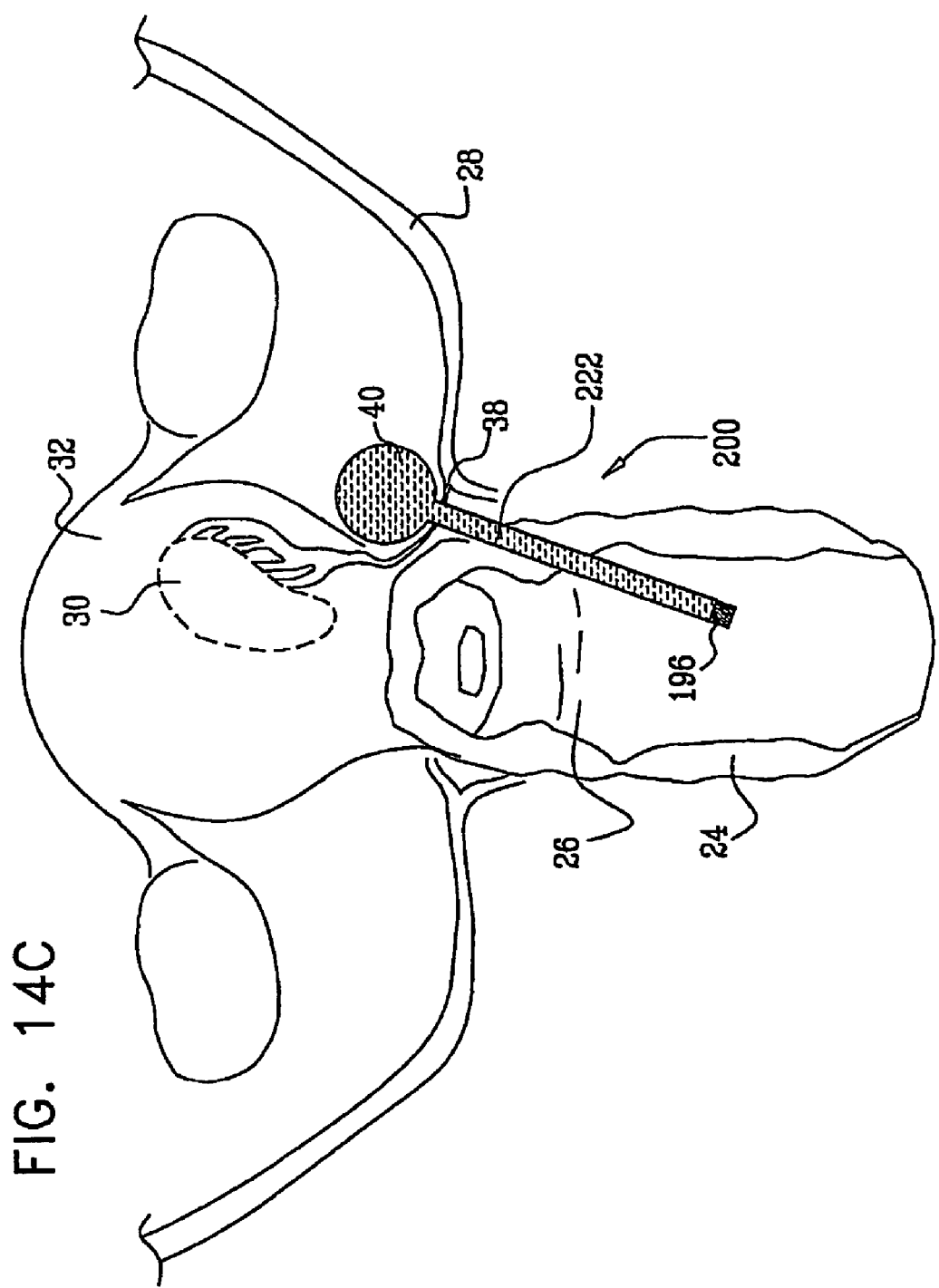

Typically, tube 222 is configured to reside in part within the patient's vagina throughout the time that balloon 40 is causing the compression of portion 38. The tube is configured to facilitate extraction of the balloon from the patient. Typically, tube 222 is flexible, and leaving the tube in the vaginal wall does not cause much discomfort to the patient. In some embodiments, tube 222 and/or balloon 40 elutes a pharmaceutical while it is disposed inside the patient, for example, the tube may elute an anesthetic or an antibiotic. FIG. 14C shows the tube in the vaginal wall of the patient after the balloon has been inflated.

FIG. 14D shows introducer 190 in greater detail, in accordance with an embodiment of the present invention. The introducer splits along lines 210 and/or 212 to facilitate the removal of the introducer from the vagina, while maintaining tube 222 (not shown) in the patient. Stopper 192 is disposed at a distance L1 from the distal end of the introducer, such that it stops the advancement of the introducer through the vaginal tissue when distal tip 191 of the introducer is disposed in the vicinity of portion 38. Distance L1 is typically between 1 cm and 2 cm, e.g., 1.5 cm. In some embodiments stopper 192 is disposed at an angle alpha of between 45 degrees and 90 degrees from the longitudinal axis of the introducer, to facilitate the correct placement of the introducer (also see alpha as shown in FIG. 14A). As appropriate, alpha may be less than 45 degrees, between 45 and 85 degrees, between 75 and 85 degrees, or essentially 90 degrees. In some embodiments, a healthcare professional chooses an introducer that is most appropriate for the proportions of the patient from a selection of introducers, the selection of introducers having different respective dimensions.

Reference is now made to FIG. 15, which is a schematic diagram of balloon 40 having a toroidal shape, disposed around the distal tip 36 of tube 22 or distal tip 236 of tube 222, in accordance with an embodiment of the present invention. In all other aspects, balloon 40 and tubes 22 and 222 are generally as described hereinabove.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
advancing a tool to a site within a patient, by penetrating vaginal tissue of the patient, the site being outside of a vagina of the patient and outside of a uterine artery of the patient, but in a vicinity of a portion of the uterine artery that supplies a uterine fibroid; and
squeezing the portion of the uterine artery with a balloon disposed at a distal tip of the tool, to an extent sufficient to occlude the uterine artery, by placing the balloon on a single side of the uterine artery and inflating the balloon, while the balloon is disposed on the single side of the uterine artery.

2. The method according to claim 1, wherein the tool includes a tube and the balloon is coupled to the tube.

3. The method according to claim 1, wherein the method does not comprise performing lumbar puncture.

4. The method according to claim 1, further comprising identifying attainment of a desired endpoint of the occluding of the uterine artery.

5. The method according to claim 4, further comprising terminating the squeezing in response to the identifying, wherein the method comprises, subsequently to the terminating, maintaining at least a portion of the tool within the patient for at least 7 days.

6. The method according to claim 1, further comprising terminating the squeezing, without active human intervention, while the tool is within the patient.

7. A method, comprising:
surgically implanting a balloon within a patient, by advancing a tool to a site within a patient, by penetrating vaginal tissue of the patient, the site being outside of a vagina of the patient and outside of a uterine artery of the patient, but in a vicinity of a portion of the uterine artery that supplies a uterine fibroid, the balloon being disposed at the distal tip of the tube;
squeezing the portion of the uterine artery with the balloon, to an extent sufficient to occlude the uterine artery, by placing the balloon on a single side of the uterine artery and inflating the balloon, while the balloon is disposed on the single side of the uterine artery; and
configuring the balloon to deflate, without human intervention, within 36 hours.

8. A method, comprising:
surgically implanting a balloon within a patient, via a vagina of the patient, by advancing a tool to a site within a patient, by penetrating vaginal tissue of the patient, the site being outside of a vagina of the patient and outside of a uterine artery of the patient, but in a vicinity of a portion of the uterine disposed at the distal tip of the tube;
squeezing the portion of the uterine artery with the balloon, to an extent sufficient to occlude the uterine artery, by placing the balloon on a single side of the uterine artery and inflating the balloon, while the balloon is disposed on the single side of the uterine artery; and
configuring the balloon to deflate without human intervention.

9. A method, comprising:
implanting a biodegradable balloon within a patient, by advancing a tool to a site within a patient, by penetrating vaginal tissue of the patient, the site being outside of a vagina of the patient and outside of a uterine artery of the patient, but in a vicinity of a portion of the uterine artery that supplies a uterine fibroid, the balloon being disposed at the distal tip of the tube; and
squeezing the portion of the uterine artery with the balloon, to an extent sufficient to occlude the uterine artery, by placing the balloon on a single side of the uterine artery and inflating the balloon, while the balloon is disposed on the single side of the uterine artery.

* * * * *